United States Patent [19]
Kolb et al.

[11] Patent Number: 5,221,616
[45] Date of Patent: Jun. 22, 1993

[54] PREVENTION OF SPONTANEOUS COMPLEMENT ACTIVATION IN MAMMALIAN BIOLOGICAL FLUIDS

[75] Inventors: William P. Kolb; Linda M. Kolb, both of Del Mar; John D. Tamerius, Carlsbad, all of Calif.

[73] Assignee: Quidel Corporation, San Diego, Calif.

[21] Appl. No.: 219,922

[22] Filed: Jul. 15, 1988

[51] Int. Cl.⁵ .............................................. C12Q 1/34
[52] U.S. Cl. ......................................... 435/18; 436/69
[58] Field of Search ............................... 435/7.9, 18

[56] References Cited

U.S. PATENT DOCUMENTS

| | | |
|---|---|---|
| 3,057,781 | 10/1962 | Mace et al. |
| 4,021,544 | 5/1977 | Nair ........................... 536/4.1 |
| 4,066,829 | 1/1978 | Nair et al. |
| 4,098,995 | 7/1978 | Nair et al. |
| 4,127,502 | 11/1978 | Li Mutti et al. |
| 4,186,192 | 1/1980 | Lundblad et al. |
| 4,232,150 | 11/1980 | Nair ........................... 536/1.1 |
| 4,258,034 | 3/1981 | Joseph et al. |
| 4,399,126 | 8/1983 | Schaub et al. |
| 4,440,758 | 4/1984 | Upeslacis et al. |
| 4,457,916 | 7/1984 | Hayashi et al. |
| 4,470,976 | 9/1984 | Miner et al. |
| 4,659,570 | 4/1987 | Terano. |

OTHER PUBLICATIONS

Mauzac et al–Chem. Abst. vol. 102 (1985) p. 160043u.
Yamada et al–Chem. Abst. vol. 102 (1985) p. 178855v.
Mochida–Chem. Abst. vol. 96 (1982) p. 11652x.
Yamada et al–Chem. Abst. vol. 104 (1986) p. 106261s.
Ziccardi, Robert J., "A New Role for C1-Inhibitor in Homeostatis: Control of Activation of the First Component of Human Complement" *J. Immun.*:128, 6 2505–2508, Jun. 1982.
Ziccardi, Robert J., "Spontaneous Activation of the First Component of Human Complement (C1) by an intracelluar Automolecular Autocatalytic Mechanism" *J. Immun.*:128, 6, 2500–2504, Jun. 1982.
Bulletin World Health Organization 39:935–938 (1968).
Bulletin World Health Organization 59:489–491 (1981).
Muller-Eberhard, H. J. Ann. Rev. Biochem. 44:697–725 (1975).
Cooper, N. R., Adv. Immunol. 37:151–216 (1985).
Schreiber, et al. Proc. Natl. Acad. Sci (USA) 75:3948–3952 (1978).
Pangburn, M. D. and Muller-Eberhard, H. J. Springer Semin. Immunopath, 7:163–192 (1984).
Tack, B. F. et al. Meth. Enzymol, 80:64–101 (1980).
Gorski, J. P. et al. J. Biol. Chem. 256:2707–2711 (1981).
Janatova, J. and Tack, B. F., Biochem. 20:2394–2402 (1981).
Harrison, R. A. et al. Proc. Natl. Acad. Sci. (USA) 78:7388–7391 (1981).
Fujita, T. et al. J. Exp. Med. 148:1044–1051 (1978).
Dahlback, B. and Hildebrand, B. Biochm. J. 209:857–863 (1983).
Hugli, T. E. Contemp. Topics Molec. Immunol. 7:181–214 (1978).

(List continued on next page.)

Primary Examiner—Sam Rosen
Attorney, Agent, or Firm—Knobbe, Martens, Olson & Bear

[57] ABSTRACT

Selected polyhydroxyl compounds, comprising monosaccharides, disaccharides and oligosaccharides, as well as certain of their derivatives, are effective in preventing the spontaneous activation of complement in vitro. The effect is enhanced in the presence of an anticoagulant together with a divalent cation chelator. Addition of these compounds makes it possible to store clinical samples at conventional temperatures from −20° to +22° C. for extended periods prior to performing complement protein assays. Effective compounds are selected through a screening protocol which comprises the use of immunoassays for complement fragments together with an algorithm for computing effectiveness. Polyhydroxyl compounds extend similar protection from activation to coagulation proteins.

22 Claims, 28 Drawing Sheets

OTHER PUBLICATIONS

Janatova, J. et al. Biochem. 19:4479-4485 (1980).
Whaley, K. and Ruddy, S. J. Exp. Med. 144:1147-1163 (1976).
Pangburn, M. K. et al. J. Exp. Med. 146:257-270 (1977).
Harrison, R. A. and Lachmann, P. J. Molec. Immunol. 17:9-20 (1980).
Ross, G. D. et al. J. Immunol. 129:2051-2060 (1982).
Fearon, D. T. and Wong, W. W. Ann. Rev. Immunol. 1:243-271 (1983).
West, C. D. et al. J. Clin. Invest. 46:539-548 (1967).
Davis, A. E. et al. J. Immunol. 132:1960-1966 (1984).
Hugli, T. E. CRC Crit. Rev. Immunol. 1:321-366 (1981).
Podack, E. R. et al. J. Immunol. 121:484-490 (1978).
Lachmann, P. J. and Thompson, R. A. J. Exp. Med. 131:643-657 (1970).
Gotze, O. and Muller-Eberhard, H. J. J. Exp. Med. 132:898-915 (1970).
Kolb, W. P. et al. J. Exp. Med. 135:549-566 (1972).
Podack, E. R. et al. J. Immuno. 120:1841-1848 (1978).
Kolb, W. P. and Muller-Eberhard, H. J. J. Exp. Med. 141:724-735 (1975).
Pangburn, M. K. and Muller-Eberhard, H. J. Exp. Med. 152:1102-1114 (1980).
Pangburn, M. K. et al. J. Exp. Med. 154:856-866 (1981).
Isenman, D. E. et al. Biochem. 20:4458-4467 (1981).
Reich, M. L. et al. Transfusion 10:14-16 (1970).
Kolmer, J. A. Amer. J. Med. Sci. 197:442-452 (1939).
Crosbie, A. and Scarbourough, H. Edinb. Med. J. 49:766-772 (1942).
Fischel et al. J. Clin. Invest. 28:1172-1181 (1949).
Muller-Eberhard, H. J. et al. J. Exp. Med. 111:201-216 (1960).
Muller-Eberhard, H. J. and Nilsson, U. J. Exp. Med. 111:217-234 (1960).
Sjoholm, A. G. and Lautrell, A. B. Clin. Exp. Immunol. 14:515-529 (1973).
Petersen, N. E. et al. Complement 2:147-153 (1985).
Rosenfeld, S. I. J. Clin. Invest. 48:2283-2292 (1969).
Hugo, F. et al. J. Immunol. Meth. 99:243-251 (1987).
Newell, S. et al. J. Lab. Clin. Med. 100:437-444 (1982).
Sundsmo, S. and Fair, D. S. Springer Semin. Immunopath. 7:379-406 (1984).
Wagner, J. L. and Hugli, T. E. Analyt. Biochem. 136:75-88 (1984).
Levch, D. L. et al. Blood Purification 4:185-193 (1986).
Chenowith, D. E. Complement 3:152-165 (1986).
Whicher, J. T. Clin. Chem. 24:7-22 (1978).
Isichei, U. P. J. Clin. Path. 32 (Suppl):117-131 (1979).
Luskin, A. T. and Tobin, M. C. Amer. J. Med. Tech. 48:749-756 (1982).
Schuur, P. H. Clin. Rheum. Dis. 1:519-543 (1975).
Schuur, P. H. and Sandson, J. N. Engl. J. Med. 278:533-538 (1986).
Sturfelt, G. and Sjoholm, A. G. Int. Arch. Appl. Immunol. 75:75-83 (1984).
Immunodiagnostics for Clinicians: Interpretation of Immunoassays M. H. Grieco and D. K. Meriney (eds.). Year Book Medical Publishers, Chicago (1983) pp. 161-142.
Clinical Guide to Laboratory Tests, N. W. Tietz (ed)., W. B. Saunders Company, Philadelphia (1983), pp. 130-142.
Experimental Immunochemistry. E. A. Kabat and M. M. Mayer (eds), Charles C. Thomas Publishing, Springfield, Ill. (1961), pp. 133-240.
Alper, C. A. et al. J. Clin. Invest. 46:2021-2034 (1967).
Charlesworth, J. A. Clin. Sci. Molec. Med. 46:223-229 (1974).
Kaplan, R. A. Arthritis Rheumatism 23:911-920 (1980).
Ruddy, S. et al. Medicine 54:165-178 (1975).
Detz, L. D. et al. Arthritis Rheumatism 20:1304-1313 (1977).
Perrin, L. H. et al. J. Clin. Invest. 56:165-176 (1975).
Perrin, L. H. et al. J. Immunol. 115:32-35 (1975).
Milgrom, H. et al. J. Immunol. 124:2780-2785 (1980).
Nitsche, J. F. Amer. J. Clin. Path. 76:679-684 (1981).
Chenowith, D. E. et al. New Engl. J. of Med. 304:497-503 (1981).
Morrow, W. J. W. et al. Annal. Rheum. Dis. 42:668-671 (1983).
Molnes, T. E. Scand. J. Immunol. 21:607-613 (1985).
Tamerius, J. D. et al. J. Immunol. 135:2015-2019 (1985).
Falk, R. F. et al. New Engl. J. Med. 312:1594-1599 (1985).
Sanders, M. E. et al. J. Immunol. 136:4456-4459 (1986).
Gawryl, M. S. et al. Arthritis Rheum. 31:188-195 (1988).
Garratty, G. Amer. J. Clin. Path. 54:531-538 (1970).
Gawryl, M. S. Fed. Proc. 46:772 (1987).

(List continued on next page.)

OTHER PUBLICATIONS

Bolotin, C. et al. Biochem. 16:2008–2015 (1977).
Hammer, C. J. et al. J. Biol. Chem. 256:3395–4006 (1981).
The Complement System. K. Rother and G. Till (eds.), Springer-Verlag, Heidelber, in press.
Kolb, W. P. et al. J. Immunol 122:2103–2111 (1979).
Cooper, N. J. et al. in Immunological Diseases. M. Samter (ed), Little Brown and Co., Boston, Mass. pp. 289–331 (1977).
Clinical Guide to Laboratory Tests, N. W. Teitz (ed) W. B. Saunders Company, Philadelphia. 1883. pp. 10 and 372.
Siverberg, M. and Kaplan, A. P. Adv. Inflammation 2:165–185 (1981).
Davis, A. E. Ann. Rev. Immunol. 6:595–628 (1988).
Polley, M. J. and Nachman, R. L. J. Exp. Med. 150:633–645 (1979).
Hugli, T. E. Contemp. Topics Molec. Immunol. 7:181–214 (1978).
Kanayama, Y. et al. J. Immunol. Meth. 88:33–36 (1986).
Kolb, W. P. et al. FASEB Journal 2:A1834 (1988).
Kolb, W. P. et al. Complement 4:181 (1987).
Mollnes, T. E. et al. Scand. J. of Immunol 22:197–202 (1985).
Falk, R. J. et al. J. Clin. Invest. 72:560–573 (1983).
Ross, G. D. and Medof, M. E. Adv. Immunol. 37:217–267 (1985).
Van Dam, A. and Hack, C. E. Complement 3:219 (1986).

FIG. 13

| Sodium Heparin (IU/mL) | Time of Incubation at 22°C (hr) | | |
|---|---|---|---|
| | 24 | 72 | 120 |
| 0 | 1.8 (61)[3] | 2.1 (52) | 3.5 (31) |
| 1 | 1.7 (64) | 1.2 (92) | 2.5 (44) |
| 5 | 1.9 (58) | 1.0 (110) | 2.0 (55) |
| 15 | 0.8 (138) | 0.8 (138) | 1.5 (73) |
| 30 | 0.8 (138) | 0.8 (138) | 1.2 (92) |
| 60 | 1.7 (64) | 1.0 (110) | 2.6 (42) |
| PBS[2] | 5.8 (19) | 15.9 (6.9) | 53.6 (2) |

| Polyhydroxyl Compound | C4d EIA (μg C4d Eq/mL) | | iC3B EIA (μg iC3b/mL) | |
| --- | --- | --- | --- | --- |
| | Treated | Untreated | Treated | Untreated |
| 2-Deoxy-D-Ribose (2M)[2] | 3.7 [70][3] | 27.4 [9] | 77.6 [7] | 139 [4] |
| Dextran 9500 (1.5M)[4] | 7.3 [27] | 21.3 [9.4] | 132 [5] | 129 [5] |
| β-D-Fructose (2M) | 3.8 [53] | 21.3 [9.4] | 14.1 [45] | 129 [5] |
| Galactose (2M) | N/D[5] | N/D | 413 [3] | 693 [1] |
| Gentiobiose (1.5M) | N/D | N/D | 22.8 [54] | 693 [1] |
| D(+) Glucosamine (0.5M) | 2.2 [91] | 21.3 [9.4] | 333 [2] | 129 [5] |
| D-Glucose (2M) | N/D | N/D | 16.4 [123] | 412 [2] |
| β-D-Glucose (2M) | 1.9 [84] | 37.6 [13] | 5.5 [96] | 112 [5] |
| Inositol (0.5M) | 7.1 [28] | 21.3 [9.4] | 189 [3] | 129 [5] |
| α-Lactose (0.5M) | 1.9 [137] | 27.4 [9] | 27.8 [21] | 139 [4] |
| β-Lactose (1M) | 3.3 [61] | 21.3 [94] | 22.2 [29] | 129 [5] |
| Maltose (1M) | 8 [25] | 21.3 [9.4] | 23.2 [28] | 129 [5] |
| D Mannitol (1.5M) | 14.9 [17] | 27.4 [9] | 272 [2] | 139 [4] |
| D Mannosamine (2M) | 1.2 [242] | 21.2 [14] | 215 [3] | 210 [3] |
| D(+) Mannose (2M) | 3.8 [68] | 27.4 [9] | 9.6 [60] | 139 [4] |
| Melibiose (1.5M) | N/D | N/D | 22.4 [63] | 693 [1] |
| Polyoxyethylene Sorbitan Monostearate (25%) | 2.7 [96] | 27.4 [9] | 148 [4] | 139 [4] |
| D(+) Raffinose (1.5M) | 7.7 [34] | 27.4 [9] | 256 [2] | 139 [4] |
| D(-) Ribose (2M) | 2.1 [124] | 27.4 [9] | 12.3 [47] | 139 [4] |
| Sedoheptulose (1.5M) | 3.6 [56] | 21.3 [9.4] | 14.8 [43] | 129 [5] |
| D-Sorbitol (2M) | 1.1 [182] | 21.3 [9.4] | 8.8 [73] | 129 [5] |
| Sucrose (1.75M) | N/D | N/D | 30.6 [48] | 412 [2] |
| Trehalose (1.5M) | N/D | N/D | 15.2 [90] | 170 [3] |
| Turanose (1.5M) | N/D | N/D | 36.7 [37] | 693 [1] |
| D(+) Xylose (2M) | 3.9 [67] | 27.4 [9] | 9.2 [63] | 139 [4] |

SEE FIG. 14B

*FIG. 14A*

| C3d, g/iC3b EIA (µG c3D,g Eq/mL) | | Bb EIA (µg Bb/mL) | | Raji CIC EIA (µg CIC Eq/mL) | |
|---|---|---|---|---|---|
| Treated | Untreated | Treated | Untreated | Treated | Untreated |
| 13.8 [14] | 22.8 [9] | 0.3 [33] | 0.5 [20] | 11.6 [103] | 13.7 [88] |
| 60.7 [3] | 21.2 [10] | 0.56 [89] | 0.34 [147] | 4.4 [70] | 3.1 [100] |
| 16.3 [13] | 21.2 [10] | 0.6 [83] | 0.34 [147] | 3.8 [82] | 3.1 [100] |
| N/D | N/D | N/D | N/D | 5.2 [131] | 1.9 [332] |
| N/D | N/D | N/D | N/D | 0.8 [267] | 1.9 [332] |
| 78.9 [3] | 21.2 [10] | 0.67 [75] | 0.34 [147] | 5.1 [61] | 3.1 [100] |
| N/D | N/D | N/D | N/D | 26 [119][6] | 13 [200][6] |
| 4.3 [77] | 70 [5] | 1.0 [130] | 1.2 [108] | 16.1 [137][6] | 34.8 [64][6] |
| 34.1 [6] | 21.2 [10] | 0.74 [68] | 0.34 [147] | 3.8 [82] | 3.1 [100] |
| 23.2 [9] | 22.8 [9] | 0 | 0.5 [20] | 12.7 [94] | 13.7 [88] |
| 3.9 [54] | 21.2 [10] | 0.45 [111] | 0.34 [147] | 3.1 [100] | 3.1 [100] |
| 8.2 [26] | 21.2 [10] | 0.31 [161] | 0.34 [147] | 4.4 [70] | 3.1 [100] |
| 69.8 | 22.8 [9] | 0.5 [20] | 0.5 [20] | 12.2 [98] | 13.7 [88] |
| N/D | N/D | 0.25 [109] | 0.38 [66] | 38.3 [23] | 13 [68] |
| 20.5 [10] | 22.8 [9] | 0.2 [50] | 0.5 [20] | 12.1 [99] | 13.7 [88] |
| N/D | N/D | N/D | N/D | 24 [108][6] | 13 [200][6] |
| 20.4 [10] | 22.8 [9] | 8.3 [1] | 0.5 [20] | 22.9 [52] | 13.7 [88] |
| 48.1 [4] | 22.8 [9] | 0.3 [33] | 0.5 [20] | 12 [100] | 13.7 [88] |
| 6.3 [32] | 22.8 [9] | 0 | 0.5 [20] | 12 [100] | 13.7 [88] |
| 23.6 [9] | 21.2 [10] | 0.67 [75] | 0.34 [147] | 3.8 [82] | 3.1 [100] |
| 6.7 [31] | 21.2 [10] | 0.45 [111] | 0.34 [147] | 3.8 [82] | 3.1 [100] |
| N/D | N/D | N/D | N/D | 1.4 [264] | 2 [350] |
| N/D | N/D | N/D | N/D | 6.6 [103] | 2 [285] |
| N/D | N/D | N/D | N/D | 2.4 [183] | 1.9 [332] |
| 15.7 [13] | 22.8 [9] | 0.3 [33] | 0.5 [20] | 12.7 [94] | 13.7 [88] |

FIG. 14B

| Biochemical Classification | Reducing Reactivity[1] | Effectiveness[2] |
|---|---|---|
| Aldopentoses | | |
| ribose | R | B |
| xylose | R | B |
| Deoxy Aldopentose | | |
| 2-Deoxy-D-Ribose | R | C |
| Aldohexoses | | |
| galactose | R | C |
| glucose | R | A |
| mannose | R | B |
| Ketohexoses | | |
| fructose | R | C |
| Aldohexosamines | | |
| glucosamine | R | C |
| mannosamine | R | C |
| Hexose Alcohols | | |
| manitol | NR | C |
| sorbitol | NR | A |
| Cyclohexanehexol | | |
| inositol | NR | C |

FIG. 15A

| Biochemical Classification | Reducing Reactivity[1] | Effectiveness[2] |
|---|---|---|
| Ketoheptose | | |
| sedoheptulose | R | C |
| Disaccharides | | |
| gentiobiose | R | B |
| α lactose | R | B |
| β lactose | R | B |
| maltose | R | C |
| melibiose | R | B |
| sucrose | NR | B |
| trehalose | NR | A |
| turanose | R | B |
| Trisaccharide | | |
| raffinote | NR | C |
| Polysaccharide | | |
| detran 9500 | NR | C |
| Nonionic Surfactant | | |
| polyoxyethylene sorbitan monostearate | -- | C |

FIG. 15B

| Incubation Time (hr) | EDTA Plasma Incubation Temp. (°C) | | EDTA Whole Blood Incubation Temp. (°C) | | Heparin Plasma Incubation Temp. (°C) | | Heparin Whole Blood Incubation Temp. (°C) | |
|---|---|---|---|---|---|---|---|---|
| | Ice | 22° | Ice | 22° | Ice | 22° | Ice | 22° |
| 0 | 4.27[2] | 4.27 | 4.27 | 4.27 | 3.53 | 3.53 | 3.53 | 3.53 |
| 1 | 3.87 | 3.16 | 3.64 | 4.73 | 3.69 | 3.29 | 4.00 | 3.47 |
| 2 | 3.78 | 4.62 | 3.22 | 7.13 | 3.71 | 3.73 | 3.80 | 3.47 |
| 3 | 4.58 | 5.36 | 5.36 | 7.31 | 3.71 | 3.98 | 4.22 | 4.04 |
| 4 | 4.18 | 5.87 | 6.67 | 8.80 | 4.11 | 3.78 | 4.64 | 4.42 |
| 5 | 4.67 | 10.0 | 6.67 | 11.98 | 4.04 | 3.96 | 4.47 | 4.51 |
| 6 | 4.20 | 14.4 | 10.27 | 13.16 | 4.07 | 3.40 | 4.18 | 3.98 |

*FIG. 16*

| Incubation Time | EDTA Plasma Donor A² | | | EDTA Whole Blood Donor A² | | | EDTA Plasma Donor B³ | | |
|---|---|---|---|---|---|---|---|---|---|
| | Incubation Temp. (°C) | | | Incubation Temp. (°C) | | | Incubation Temp. (°C) | | |
| (hr) | Ice | 4° | 22° | Ice | 4° | 22° | 4° | 22° | 37° |
| 0 | 2.69 | 2.69 | 2.61 | 2.67 | 2.67 | 2.67 | 8.3 | 8.4 | 8.5 |
| 1 | 2.80 | 2.61 | 2.61 | 2.38 | 2.38 | 2.38 | 7.6 | 8.2 | 8.4 |
| 2 | 3.36 | 2.91 | 3.01 | 2.67 | 2.47 | 2.88 | 8.4 | 8.6 | 12.5 |
| 3 | 2.61 | 2.61 | 2.61 | 2.99 | 3.11 | 2.57 | 8.0 | 9.0 | 18.0 |
| 4 | 2.43 | 3.01 | 2.80 | 2.47 | 2.99 | 2.88 | 7.8 | 9.9 | 54.4 |
| 5 | 3.13 | 2.71 | 3.01 | 3.91 | 2.99 | 3.62 | 8.2 | 10.8 | 128.2 |
| 6 | 2.61 | 2.71 | 4.17 | 3.76 | 3.53 | 3.62 | 8.0 | 10.6 | 306.0 |
| 24 | 3.36 | 4.82 | 33.86 | 7.19 | 15.42 | 37.09 | 9.5 | 38.8 | >400 |

FIG. 17

EDTA Plasma

| Incubation Time (Days) | Incubation Temp. (°C) | | | |
|---|---|---|---|---|
| | -20° | 4° | 22° | 37° |
| 0 | 1.7 | 1.7 | 1.7 | 1.7 |
| 1 | 1.3 | 1.0 | 1.0 | 0.7 |
| 2 | 1.3 | 1.1 | 1.2 | 0.9 |
| 3 | 1.4 | 1.7 | 1.6 | 1.3 |
| 4 | 0.6 | 1.2 | 0.9 | 1.0 |
| 5 | 1.3 | 1.4 | 1.2 | 1.1 |
| 6 | 1.2 | 0.7 | 1.3 | 1.3 |
| 7 | 1.3 | 1.1 | 0.9 | 1.0 |

FIG. 18

| Specimen | C4d EIA (μg C4d Eq/mL) | | iC3b EIA (μg iC3b/mL) | | C3d, g/iC3b EIA (μg C3d, g Eq/mL) | | Bb EIA (μg Bb/mL) | | Raji CIC EIA (μg CIC Eq/mL) | |
|---|---|---|---|---|---|---|---|---|---|---|
| | Sol B | PBS | Sol B | PBS | Sol B | PBS | Sol B | PBS | Sol B | PBS |
| NHS | 7.4[2] | 69.8 | 13.0 | 71.8 | 3.2 | 58.9 | 9.8 | 9.9 | 2.0 | 0.32 |
| | (120) | (13) | (95) | (17) | (109) | (11) | (114) | (108) | (105) | (390) |
| NHP | 7.1 | 21 | 8.2 | 20.9 | 1.7 | 12 | 8.8 | 9.4 | 0.71 | 0.47 |
| | (103) | (39) | (88) | (34) | (65) | (29) | (111) | (117) | (100) | (172) |
| Plasma from Whole Blood | 7.2 | 21 | 7.2 | 20.9 | 1.2 | 12 | 10.2 | 9.4 | 0.78 | 0.47 |
| | (99) | (39) | (100) | (34) | (67) | (29) | (91) | (117) | (96) | (172) |
| Whole Blood | 6.9 | 30 | 10.1 | 22.6 | 1.5 | 21.8 | 8.7 | 10.2 | 0.73 | 0.71 |
| | (97) | (25) | (86) | (38) | (80) | (17) | (121) | (111) | (101) | (132) |

FIG. 19

Complement Fragment Measured

| Pre-Dilution Factor | C4d | | | | | | C3d, g/iC3b[3] | | | | | |
|---|---|---|---|---|---|---|---|---|---|---|---|---|
| | Untreated | | | Treated | | | Untreated | | | Treated | | |
| | Incubation Time (hr) | | | Incubation Time (hr) | | | Incubation Time (hr) | | | Incubation Time (hr) | | |
| | 0 | 24 | 48 | 0 | 24 | 48 | 0 | 24 | 48 | 0 | 24 | 48 |
| 0 | 5.1 | 25.2 | 39.6 | 5.8 | 5.0 | 5.4 | 2.7 | 10.2 | 13.7 | 2.8 | 2.7 | 3.0 |
| 1:2 | 4.8 | 25.8 | 42.3 | 4.6 | 5.0 | 5.2 | 4.2 | 5.9 | 7.9 | 3.4 | 4.0 | 5.1 |
| 1:3 | 4.9 | 26.7 | 44.4 | 5.0 | 5.2 | 5.0 | 6.0 | 7.6 | 11.3 | 4.3 | 5.0 | 5.6 |
| 1:4 | 5.2 | 26.3 | 40.8 | 4.9 | 4.9 | 4.9 | 7.8 | 9.8 | 13.0 | 5.0 | 6.2 | 7.4 |
| 1:5 | 4.7 | 29.6 | 41.2 | 5.2 | 5.2 | 5.2 | 12.0 | 18.0 | 18.5 | 8.0 | 9.1 | 13.2 |

FIG. 20

| Complement Component Studied | Complement-Containing Sample ||||||||||
| --- | --- | --- | --- | --- | --- | --- | --- | --- | --- | --- |
| | EDTA-Plasma |||||| Heparin-Plasma ||| EDTA-Whole Blood |||
| | Incubation Temp. (°C) |||||| Incubation Temp. (°C) ||| Incubation Temp. (°C) |||
| | -20° | Ice | 4° | 22° | 37° | -20° | Ice | 4° | 22° | -20° | Ice | 4° | 22° |
| C4 | >7d[1] | 2h[2] | --[3] | 2h | -- | -- | -- | -- | >6<24h | -- | 2h | -- | <1h |
| C3 | 0[4] | 6h | 6h | 3h | 1h | -- | >6<24h | -- | -- | 0 | 4h | 4h | 3h |
| Factor B | >7d | >7d | >7d | >7d | >7d | -- | -- | -- | -- | -- | -- | -- | -- |
| C5 through C9[5] | >7d | >7d | >2d | 4h | -- | -- | -- | -- | -- | -- | -- | -- | -- |

FIG. 21

| Complement Component Studied | Complement-Containing Sample | | | | | | | | | | | |
|---|---|---|---|---|---|---|---|---|---|---|---|---|
| | EDTA–Plasma Incubation Temp. (°C) | | | | Heparin–Plasma Incubation Temp. (°C) | | | | EDTA–Whole Blood Incubation Temp. (°C) | | | |
| | -20° | Ice | 4° | 22° | -20° | Ice | 4° | 22° | -20° | Ice | 4° | 22° |
| C4 | >30d[1] | >10d | >7d | 5d | >30d | >2d | >2d | >2d | -- | -- | -- | -- |
| C3 | >30d | >10d | >7d | >7d | >30d | >2d | >2d | >2d | -- | >2d | >2d | >2d |
| Factor B | >30d | >10d | >7d | >7d | --[2] | -- | -- | -- | -- | -- | -- | -- |
| C5 through C9 | >30d | >10d | >7d | >2d | -- | -- | -- | -- | -- | -- | -- | -- |

FIG. 22

PREVENTION OF SPONTANEOUS COMPLEMENT ACTIVATION IN MAMMALIAN BIOLOGICAL FLUIDS

BACKGROUND OF THE INVENTION

The complement System of Plasma Proteins

Complement (C) is a cascading system of circulating blood plasma proteins. The C system consists of 20 different proteins, inclusive of the naturally occurring modulators of C activity, which collectively represent approximately 15% of the globulin fraction of normal human serum, H. J. Muller-Eberhard, Ann. Rev. Biochem. 44:697-725 (1975); K. B. Reid and R. R. Porter, Ann. Rev. Biochem. 50:433-464 (1981). In general C components are present in circulating blood plasma as non-activated native proteins. Complement components are activated sequentially upon the conversion of an inactive zymogen to an active proteolytic enzyme capable of cleaving, and thereby activating the next component in the reaction sequence. Polypeptide fragments of C proteins produced as tne result of cleavage by C enzymes, as well as subcomponents of the C1 complex, are designated by a small letter, e.g., the third component of C (C3) is cleaved to C3a and C3b -polypeptides as the result of C activation, Bull. W.H.O. 39:935-938 (1968); Bull. W.H.O. 59:489-491 (1981).

C activation can be initiated or triggered via two distinct and separate pathways termed the classical and alternative C activation pathways, H. J. Muller-Eberhard, Ann. Rev. Biochem. 44:697-725 (1975); M. K. Pangburn and H. J. Muller-Eberhard, Springer Semin. Immunopath. 7:163-192 (1984). The proteins unique to the classical C pathway are C1, C4 and C2. The C1 component is present in circulating blood plasma as a calcium dependent complex of subcomponents C1q, C1r and C1s which are present in the C1 complex in molar ratios of 1:2:2, respectively, N. R. Cooper, Adv. Immunol. 37:151-216 (1985). Classical C pathway activation is triggered upon binding of the C1q subcomponent of C1 to IgG or IgM immunoglobulin containing antigen-antibody complexes (immune complexes) or to a wide variety of biologically relevant activating substances, N. R. Cooper, Adv. lmmunol. 37:151-216 (1985).

Complement proteins unique to the alternative C activation pathway are Factors B, D and P (Properdin). However, C3 and the complement regulatory proteins Factor H and Factor I, although not unique to the alternative pathway, are usually considered to be alternative pathway components since they are required for full functional alternative pathway activation to occur, R. D. Schreiber, et al., Proc. Natl. Acad. Sci. (USA) 75:3948-3952 (1978); M. K. Pangburn and H. J. Muller-Eberhard, Springer Semin. Immunopath. .7:163-192 (1984). Alternative C pathway activation can be triggered by IgA-immunoglobulin containing immune complexes, or a variety of fungal, viral, parasitic or gram negative bacterial surface determinants.

C4 activation is a key reaction step in triggering the classical C pathway. The C4 present in circulating blood plasma is a 200,000 molecular weight (MW) protein comprised of three disulfide bonded subunits, $\alpha$-93,000 MW, $\beta$-75,000 MW, $\gamma$-32,000 MW, B. F. Tack et al., Meth. Enzymol. 80:64-101 (1980). The $\alpha$-subunit of native C4 contains an intra-chain, internal, active thiol ester bond which is normally shielded or inaccessible to nucleophilic attack by solvent water molecules. C4 is activated by the C1s proteolytic enzyme. C1s cleaves the C4 $\alpha$-chain at peptide bond 77 resulting in the production of C4a and C4b fragments. The C4a fragment, a 9000 MW peptide, is one of the C anaphylatoxins, J. P. Gorski, et al., J. Biol. Chem. 256:2707-2711 (1981). Cleavage of the C4 $\alpha$-chain by C1s, with resultant release of the C4a peptide, exposes the internal, active thiol ester bond present in the larger C4b fragment to nucleophilic attack by target surface acceptor molecules (amino or hydroxyl chemical groups) or by solvent water molecules. The successful nucleophilic attack by a target acceptor molecule, which must occur within milliseconds after C4 $\alpha$-chain cleavage by C1s, results in the formation of a covalent ester bond between the C4b fragment and the target surface, J. Janatova and B. F. Tack, Biochem. 20:2394-2402 (1981); R. A. Harrison, et al., Proc. Natl. Acad. Sci. (USA) 78:7388-7392 (1981). Approximately 10% of nascent C4b fragments will bind to target acceptor molecules While the remaining 90% will react with the hydroxyl chemical group of solvent water. The C4b fragments which have reacted with water are unable to subsequently bind to target surface acceptors and accumulate in the fluid phase reaction solution as inactive by-products of the classical pathway activation event.

Both target acceptor bound and fluid-phase C4b fragments are subject to further fragmentation and degradation reactions as the result of normal physiological control mechanisms. Thus, the C4b $\alpha$-chain of surface-bound and fluid-phase C4b is degraded to C4c and C4d fragments by the naturally occurring C regulatory proteins C4 Binding Protein (C4BP) and Factor I. C4BP acts as a required cofactor which must bind to the C4b fragment before Factor I mediated cleavage can occur, T. Fujita, et al., J. Exp. Med. 148:1044-1051 (1978); B. Dahlback and B. Hildebrand, Biochem. J. 209:857-863 (1983). C4c and C4d fragments have molecular weights of 146,000 and 45,000, respectively. The C4d fragment is derived from the portion of the C4 $\alpha$-chain containing the active thiol ester site.

Activation of C3 is the first reaction step shared by both C pathways. Thus, not only is C3 the most abundant protein of the C system (the normal human plasma concentration of C3 is 1200 $\mu$g/mL), it is also a very centrally important component in the C activation sequence. The C3 convertase enzymes of either C pathway, i.e., the C4b,2a enzyme of the classical or the C3b,Bb enzyme of the alternative pathway, cleaves the C3 $\alpha$-chain at peptide bond 77 resulting in the production of C3a and C3b fragments. The C3a fragment is one of the C anaphylatoxins, T. E. Hugli, Contemp. Topics Molec. Immunol. 7:181-214 (1978). The $\alpha$-chain of the larger C3b fragment also contains an intra-chain, internal, active thiol ester bond which becomes accessible to nucleophilic attack by target surface acceptor molecules or by solvent water molecules. The successful nucleophilic attack by a target acceptor molecule, which must occur within milliseconds after C3 $\alpha$-chain cleavage, results in the formation of a covalent ester bond between the C3b fragment and the target surface, J. Janatova, et al., Biochem. 19:4479-4485 (1980). Analogous to C4, approximately 10% of nascent C3b fragments will bind to target acceptors while the remaining 90% react with solvent water molecules. The C3b fragments which have reacted with water are unable to subsequently bind to target surface acceptors and they therefore accumulate in the fluid phase reaction solution as inactive by-products of any C activating event.

As part of normal physiological control mechanisms, both acceptor bound and fluid phase C3b fragments are subject to further fragmentation and degradation reactions. Thus, the C3b α-chain of surface bound or fluid phase C3b is degraded to iC3b and C3f fragments by the naturally occurring C regulator proteins, Factors H and I. Factor H acts as a required cofactor which must bind to the C3b fragment before Factor I mediated cleavage can occur, K. Whaley and S. Ruddy, J. Exp. Med. 144:1147–1163 (1976); M. K. Pangburn, et al., J. Exp. Med. 146:257–270 (1977); R. A. Harrison and P. J. Lachmann, Molec. Immunol. 17:9–20 (1980); G. D. Ross, et al., J. Immunol. 129:205–2060 (1982). The iC3b fragments can be further degraded by a variety of proteolytic enzymes, e.g., Factor I in the presence of the CRI C receptor, trypsin, elastase or plasmin, resulting in the production of C3c and C3d,g ($\alpha_2$D) fragments, D. T. Fearon and W. W. Wong, Ann. Rev. Immunol. 1243–271 (1983). The C3d,g ($\alpha_2$D) fragment appears to be the final C3 degradation fragment normally produced in circulating blood plasma, C. D. West, et al., J. Clin. Invest. 46:539–548 (1967); A. E. Davis, et al., J. Immunol. 132:1960–1966 (1984). However, C3d,g can be further degraded in extravascular sites of inflammation by a variety of proteolytic enzymes to yield C3d and C3g fragments. The molecular weights of the various physiological degradation fragments of C3 are: iC3b-185,000; C3f-2300; C3c-145,000, C3d,g-40,000; C3d-30,000, C3g-10,000.

Activation of either C pathway through the C3 step results in assembly of C5 activating enzymes, also termed C5 convertase enzymes. The classical and alternative pathway C5 convertase enzymes are C4b,2a,3b and C3b,Bb,C3b, respectively. Both C5 convertase enzymes cleave the C5 α-chain at peptide bond 74 resulting in the production of C5a and C5b fragments. The C5a fragment is one of the C anaphylatoxins, T. E. Hugli, CRC Crit. Rev. Immunol. 1:321–366 (1981). The larger C5b fragment remains bound to the C5 convertase enzyme which produced it, and upon interaction with C6 and C7 a C5b,6,7 complex is formed which becomes bound to the target surface, E. R. Podack, et al., J. Immunol. 121:484–490 (1978). The C5b,6,7 complex subsequently binds C8 and multiple C9 molecules leading to C5b-9 complex assembly. It is the assembled C5b-9 complex which is responsible for the irreversible target membrane surface damage associated with C activation, P. J. Lachmann and R. A. Thompson, J. Exp. Med. 131:643–657 (1970); O. Gotze and H. J. Muller-Eberhard, J. Exp. Med. 132:898–915 (1970); W. P. Kolb, et al., J. Exp. Med. 135:549–566 (1972). The C5b fragment, unlike C4b and C3b, does not contain an intra-chain thiol ester bond and is not degraded by Factor I nor any other known physiologically occurring plasma enzyme or inhibitor. However, plasma inhibitors do exist to protect bystander target surfaces from nascent C5b,6,7 complex binding and subsequent C5b-9 complex assembly. The major inhibitor of bystander cell membranolysis mediated by the terminal C components is the naturally occurring blood plasma protein termed S-protein, E. R. Podack, et al., J. Immunol. 120:1841–1848 (1978). Since S-protein binds at the C7 stage of terminal complex assembly, a significant percentage of C5 activation events result in the formation of SC5b,6,7 complexes in free solution. SC5b-7 complexes combine with C8 and multiple C9 molecules to produce a fluid-phase SC5b-9 complex as an inactive by-product of C5 through C9 terminal pathway activation, W. P. Kolb and H. J. Muller-Eberhard, J. Exp. Med. 141:724–735 (1975).

Forms of Spontaneous C Activation In Vivo

In contrast to the defined sequential reaction steps outlined above for activation of the classical C pathway, i.e., triggered as the result of C1 binding to a specific initiator substance, activation of the alternative C pathway is dependent upon naturally occurring spontaneous forms of C activation.

Many studies have reported the occurrence of low levels of spontaneous C3 activation in aqueous solution. Thus the internal thiol ester bond present in C3 is subject to protracted spontaneous nucleophilic attack and scission by solvent water or small amines resulting in the formation of modified C3 molecules, C3($H_2O$), also termed C3i, possessing all of the functional properties of C3b, M. K. Pangburn and H. J. Muller-Eberhard, J. Exp. Med. 152:1102–1114 (1980); M. K. Pangburn, et al., J. Exp. Med. 154:856–866 (1981). Thus C3($H_2O$) has been shown to bind Factor B in the presence of Mg++ and, together with Factor D, to form the fluid-phase C3 convertase, C3($H_2O$),Bb(Mg), of the alternative pathway, M. K. Pangburn and H. J. Muller-Eberhard, Springer Semin. Immunopathol. 7:163–192 (1984). Even though the fluid phase C3($H_2O$),Bb(Mg) alternative pathway C3 convertase is highly susceptible to inhibitory dissociation regulation by Factors H and I, the reaction kinetics indicate the C3($H_2O$) has a temporarily greater chance to form the fluid phase C3 convertase then to be enzymatically degraded by Factor H and I, D. E. Isenman, et al., Biochem. 20:4458–4467 (1981). Therefore, low levels of spontaneous modification and scission of C3 internal thiol ester bonds, with the resultant formation of fluid-phase alternative pathway C3 convertases with the ability to generate C3a and C3b activation fragments, undoubtedly occurs in vivo due to the presence of sufficiently high concentrations of nucleophilic amines e.g., ammonia, methylamine, ethylamine and free amino acids in blood plasma, M. K. Pangburn and H. J. Muller-Eberhard, Springer Semin. Immunopathol. 7:163-192 (1984). The occurrence of spontaneous C3 activation can be quantitated directly using newly developed monoclonal antibody based enzyme immunoassays which demonstrate clearly iC3b and C3d,g fragments to be present in freshly drawn EDTA, citrate or heparin normal human plasma as described below in the Analytical Methods and Examples sections.

A similar situation appears to be true for the production of C4 activation fragments in vivo as the result of spontaneous C4 internal thiol ester bond hydrolysis and scission as evidenced by the measurement of significant levels of C4d related fragments in freshly drawn normal human plasma (NHP) (see the Analytical Methods and Examples sections below).

Forms of Spontaneous C Activation In Vitro

Since the discovery of the C system, investigators have observed and documented the "spontaneous" loss of C activity in serum or plasma samples stored in vitro. Early definitions of the complement system invariably included a statement about the lability of C present in serum or plasma stored at 4° C. or at room temperature (22° C.), M. L. Reich, et al., Transfusion 10:14–16 (1970). For example, in 1939, Kolmer reported that of six citrated plasma samples stored at 4° C. for 14 days, two lost 50% of their original hemolytic C activity, three lost 66% and one lost 80%, J. A. Kolmer, Amer. J. Med. Sci. 197: 442–452 (1939). In 1942, Crosbie and Scarborough reported as much as 50% loss of C activity in citrated plasma samples stored at 4 C for 2 days and greater than a 75% loss of C activity was observed by day 12, A. Crosbie and H. Scarborough, Edinb. Med. J. 49:766–772 (1942). Fischel, et al. subsequently reported that even when stored frozen at −17° C., normal human serum samples lost 25 to 33% of their original C activity after 7 days, E. E. Fischel, et al., J. Clin. Invest. 28:1172–1181 (1949). Therefore, the storage of serum and plasma samples under conditions allowing for the retention of full C activity has always been a problem for basic research as well as clinical laboratories.

1. Spontaneous Production of C Activation Fragments and Complexes in Serum Samples Stored In Vitro Historically, as the individual C component proteins were isolated and characterized immunochemically and biochemically, the changes occurring to the C system of proteins as the result of spontaneous decay activation due to in vitro storage were defined. Thus, in 1960, Muller-Eberhard and co-workers, using one-dimension immunoelectrophoretic procedures, demonstrated that upon storage of fresh normal human serum (NHS) at 1° C. for 30 days or 37° C. for two days, the third component of complement (C3, $\beta_1C$) was fragmented completely to $\beta_1A$ ($\beta_1A$ is now known to be the C3c physiological breakdown fragment of C3), H. J. Muller-Eberhard, et al., J. Exp. Med. 111:201–216 (1960). The conversion of $\beta_1C$ to $\beta_1A$ paralleled the loss of C3 functional activity during the time course of in vitro storage, H. J. Muller-Eberhard and U. Nilsson, J. Exp. Med. 111:217–234 (1960). Storage of fresh NHS at room temperature (22° C.) for 24 hr also results in the fragmentation of C4 to the physiological split products C4c and C4d as evaluated by two-dimension immunoelectrophoretic procedures, A. G. Sjoholm and A. B. Lautrell, Clin. Exp. Immunol. 14:515–529 (1973); N. E. Petersen, et al., Complement 2:147–153 (1985). In these studies, the fragmentation of C4 in NHS was shown to be the result of the in vitro storage procedure and not due to artifactual C4 activation which can occur during the electrophoresis procedure if EDTA is not added to the specimen, agar or agarose and all buffer solutions, S. I. Rosenfeld, J. Clin. Invest. 48:2283–2292 (1969). In addition to the spontaneous activation of C3 and C4, incubation of NHS at 37° C. for one hour also results in the production of SC5b-9 complexes, as measured by a sensitive enzyme immunoassay (EIA), to levels which are as much as 10-fold higher than the SC5b-9 complex concentration present in non-incubated control samples, F. Hugo, et al., J. Immunol. Meth. 99:243–251 (1987).

Many theories have been proposed to explain the mechanism of spontaneous C activation in serum as the result of in vitro storage. For example, the formation of immunoglobulin aggregates at 1°–4° C. (cryoglobulin precipitates) in normal or patient serum specimens can result in classical C pathway activation and formation of C fragments even at 4° C., S. Newell, et al., J. Lab. Clin. Med. 100:437–444 (1982). Immunoglobulins present in NHS can also form aggregates, which would be expected to mediate classical pathway activation, as the result of surface contact-denaturation, prolonged storage in solution, or as the result of freeze-thawing. Activation and fragmentation of C components can also be mediated by a number of coagulation enzymes formed as the result of in vitro clot formation during the procedure required to prepare serum, J. S. Sundsmo and D. S. Fair, Springer Semin. Immunopath. 7:379–406 (1984). The ability of coagulation enzymes to cleave various C proteins was clearly documented in the report of Wagner and Hugli in which the levels of all three C anaphylatoxins (C4a, C3a, C5a) in freshly drawn NHS were elevated significantly as compared with the anaphylatoxin levels measured in matched EDTA-plasma samples, J. L. Wagner and T. E. Hugli, Analyt. Biochem. 136:75–88 (1984). In addition, spontaneous C4 and C3 internal thiol ester bond hydrolysis reactions would also contribute significantly to the loss of C activity and the production of complement component fragments during storage in vitro (also refer to the Examples section for direct quantitative data concerning the spontaneous activation of complement during the storage of serum in vitro).

2. Spontaneous Production of C Activation Fragments and Complexes in Plasma Samples Stored In Vitro Many, but not all, of the C activating events described above which occur during the storage of serum in vitro can be avoided by preparing EDTA or citrated plasma samples instead of serum. EDTA and citrate inhibit the activation of the coagulation system of plasma protein enzymes by combining with and thereby functionally removing calcium ions from the collected blood samples. Thus, these calcium ion chelators prevent the formation of activated coagulation enzymes which can contribute directly to the production of C fragments in serum as described above. In addition, EDTA and citrate inhibit the in vitro activation of C since both the classical and alternative C activation pathways have divalent cation-requiring ($Ca^{++}$, $Mg^{++}$) reaction steps which are inhibited in the presence of EDTA or citrate. Therefore, EDTA or citrated plasma samples are currently used routinely instead of serum samples for studies designed to quantitate C component or fragment levels in freshly drawn patient specimens, S. Newell, et al., J. Lab. Clin. Med. 100:437–444 (1982); J. L. Wagner and T. E. Hugli, Analyt. Biochem. 136:75–88 (1984).

Heparinized plasma is not routinely used as a specimen for C studies since heparin does not functionally remove divalent cations from the plasma specimens being prepared. Therefore, C activation can occur uninhibited in heparinized whole blood or plasma during many in vitro procedures, D. L. Levch, et al., Blood Purification 4:185–193 (1986); D. E. Chenoweth, Complement 3:152–165 (1986). However, if proper collection and storage procedures are utilized, heparinized plasma samples will provide the same C component and activation fragment quantitative profiles as plasma collected in EDTA or citrate. (This point will be discussed further in the Detailed Description of the Invention and Examples sections of this application).

Even though spontaneous C activation in stored plasma samples is less of a problem than in serum samples, spontaneous C activation does occur in plasma samples stored in vitro. Therefore the C4d fragment concentration, as measured by intermediate gel-rocket immunoelectrophoresis, in EDTA-normal human plasma samples stored at 20° C. for 24 hours increased by 3–4 fold as compared with the original C4d values, N. E. Petersen, et al., Complement 2:147–155 (1985).

Why is the Spontaneous In Vitro Activation of the C System a Problem?

Activation and consumption of individual C components occurs in many human diseases as the result of specific in vivo C fixation events. Therefore, C component measurements in patient plasma or serum samples are used routinely as a diagnostic tool to measure the severity of certain diseases or to monitor disease progress. C component measurements appear to be most useful in the case of patients with overt circulating immune complex (CIC) diseases in which the classical pathway components C1, C4 and C2, as well as C3, are frequently, but variably, reduced when measured by immunochemical or functional titration procedures, J. T. Whicher, Clin. Chem. 24:7-22 (1978); U. P. Isichei, J. Clin. Path. 32(Suppl):117-121 (1979). Thus, serum sickness, clinically severe systemic lupus erythematosus (SLE), chronic active hepatitis, some cases of mixed connective tissue disease and rheumatoid vasculitis are examples of human immune complex diseases which routinely show evidence of classical C pathway activation, i.e., plasma or serum samples from these patients frequently contain decreased concentrations of C1, C4 and C3 C components and reduced CH50 functional C activity levels, A. T. Luskin and M. C. Tobin, Am. J. Med. Tech. 48:749-756 (1982); P. H. Schur, Clin. Rheum. Dis. 1:519-543 (1975). In the case of SLE, significant correlations between C assay results and renal pathology have been documented, P. H. Schur and J. Sandson, N. Engl. J. Med. 278:533-538 (1968); G. Sturfelt and A. G. Sjoholm, Int. Arch. Appl. Immunol. 75:75-83 (1984). Severe nephritis in the SLE patient is almost always preceded or accompanied by reductions in serum levels of C4 or C3, or both, In: *Immunodiagnostics for Clinicians: Interpretation of Immunoassays*. M. H. Grieco and D. K. Meriney (eds). Year Book Medical Publishers, Chicago (1983) pp. 161-186.

Plasma or serum samples collected from patients with a number of different diseases can also show evidence of alternative C pathway activation and consumption in vivo. Thus, plasma or serum samples obtained from patients with post-streptococcal glomerulonephritis, membranoproliferative glomerulonephritis (MPGN), particularly in association with C3-nephritic factor production, and gram-negative bacteremia, show decreased levels of C3 and variably decreased levels of Factor B, with normal levels of C4, J. T. Whicher, Clin. Chem. 24:7-22 (1978); A. T. Luskin and M. C. Tobin, Am. J. Med. Tech. 48:749-756 (1982).

Until recently, the measurement of individual C component levels in human plasma or serum samples has been performed primarily by using radial immunodiffusion or nephelometric procedures, In: *Clinical Guide to Laboratory Tests*. N. W. Tietz (ed)., W. B. Saunders Company. Philadelphia (1983), pp. 130-142.

These procedures are simple to conduct, relatively inexpensive and, since they measure the levels of total antigen present in a sample, no special procedure is required in the collection and storage of specimens. However, tests which measure C functional activity, e.g., the traditional CH50 assay, do require special collection and storage procedures. Thus, it is normally recommended that plasma or serum samples which are to be used in the CH50 test should be stored at 4° C. and assayed within 4-8 hours after collection. If the specimens can not be tested within this 4-8 hour time period, they should be stored frozen at $-70°$ C. or below in an effort to prevent spontaneous C activation and consumption from occurring in vitro, In: *Clinical Guide to Laboratory Tests*. N. W. Tietz (ed), W. B. Saunders Company, Philadelphia (1983), pp. 130-142; In: *Experimental Immunochemistry*. E. A. Kabat and M. M. Mayer (eds), Charles C. Thomas Publishing, Springfield, Illinois (1961), pp. 133-240.

During the past 20 years, a large number of studies have been published indicating that the measurement of individual C component total antigen levels in patient plasma or serum samples has several severe limitations as a technique to provide information regarding in vivo C activation. Determination of the fractional catabolic rate (FCR) of individual C components in vivo is the best available procedure to study abnormalities in complement activation and metabolism in different disease states. The FCR is determined from circulating blood plasma clearance curves after intravenous injection of a highly purified, radiolabeled C component under investigation. Over 150 studies have been conducted to determine the metabolic behavior of C3, C4, C5 and Factor B in humans. Thus, in normal subjects the mean FCR rate for C3 has been determined to be 1.3 to 2.0% of the plasma pool/hr, C. A. Alper, et al., J. Clin. Invest. 46:2021-2034 (1967 ; J. A. Charlesworth, Clin. Sci. Molec. Med. 46:223-229 (1974). The FCR for C4 in normals has been determined to be 1.7 to 2.3% of the plasma pool/hr, R. A. Kaplan, Arthritis Rheumatism 23:911-920 (1980). The FCR for C5 in normals has been determined to be 1.6 to 2.2% of the plasma pool/hr, S. Ruddy, et al., Medicine 54:165-178 (1975). The FCR for Factor B in normals has been determined to be 1.4 to 1.9% of the plasma pool/hr, R. A. Kaplan, et al., Arthritis Rheumatism 23:911-920 (1980). These results indicate that all four C proteins are among the most rapidly metabolized of all plasma proteins in normal human subjects. Studies of C component metabolism have also been conducted in a variety of human diseases. For example, hypercatabolism of C components has been observed routinely in patients with renal allografts, glomerulonephritis, SLE, rheumatoid arthritis, acquired hemolytic anemia, hereditary angioedema, hypogammaglobulinemia and multiple myeloma, S. Ruddy, et al., Medicine 54:165-178 (1975); C. A. Alper, et al., J. Clin. Invest. 46:2021-2034 (1967); L. D. Detz, et al., Arthritis Rheumatism 20:1304-1313 (1977); R. A. Kaplan, Arthritis Rheumatism 23:911-920 (1980). The pathologic hypercatabolism of C components observed in these diseases was expected based on immunopathologic studies and marked reduction in serum total antigen levels for the C3, C4 and Factor B components present in many patients with these diseases. However, these studies also clearly demonstrated that hypercatabolism of C3, C4 and Factor B occurred routinely in many patients even when total antigen plasma levels were maintained within the normal range, S. Ruddy, et al., Medicine 54:165-178 (1975). Therefore, a significant percentage, if not the majority, of patients with a variety of autoimmune diseases are able to increase C3, C4 and Factor B synthetic rates in order to maintain normal plasma levels of these C proteins despite the occurrence of hypercatabolism and consumption of C due to their underlying disease states. Clearly in these cases the radial immunodiffusion (RID) and nephelometric type procedures that measure total plasma antigen levels are unable to detect abnormally high levels of C activation and consumption occurring in these patients.

Because of this limitation inherent in measuring total antigen levels of individual C proteins in patient plasma samples, and since it is impractical to conduct C component metabolic studies on every patient, clinical investigators have become increasingly interested in measuring directly the levels of complement activation products which are present in patient plasma samples as a procedure to more clearly assess the extent of C activation and consumption occurring in vivo in any given patient.

The first of the C activation fragment assays were described by Lambert and coworkers in 1975 who reported: (1) elevated plasma levels of C3d (C3d,g) fragments were observed in 68% of SLE patients (n=41), in 87% of patients with MPGN (n=31), in 62% of patients with hypocomplementemic nephritis (n=26) and in 15% of patients with normocomplementemic nephritis (n=13); (2) significantly elevated plasma levels of Ba fragments were found in 46% of SLE patients (n=41), in 67% of MPGN patients (n=31) and in 50% of patients with hypocomplementemic nephritis (n=26); and (3) elevated levels of C4d fragments were measured in synovial fluids from patients with seropositive (RA+) as well as seronegative (RA−) rheumatoid arthritis as compared to synovial fluids obtained from patients with degenerative joint disease. The quantities of C4d fragments measured in the RA+ synovial fluids was significantly elevated over the C4d fragment concentrations in synovial fluids from RA− patients. These first studies employed polyethylene glycol (PEG) precipitation of all high MW proteins from the plasma or synovial fluid specimens, and the supernatants were analyzed by RID procedures to quantitate the C3d,g, Ba and C4d fragments, L. H. Perrin, et al., J. Clin. Invest. 56:165–176 (1975); L. H. Perrin, et al., J. Immunol. 115:32–35 (1975).

Evidence of classical C pathway activation in vivo has also been demonstrated in a number of diseases using a rocket immunoelectrophoretic procedure to measure C4 activation by determining a C4d/C4 ratio. Using this procedure, elevated plasma C4d/C4 ratios were measured in plasma samples from several patients with rheumatoid arthritis, hereditary angioedema, SLE and chronic urticaria with hypocomplementemia. These studies also indicated that the C4d/C4 ratio correlated significantly with the in vivo metabolism of radiolabeled C4 in these rheumatoid arthritis (RA) patients (n=12), H. Milgrom, et al., J. Immunol. 124:2780–2785 (1980). Subsequently, additional studies indicated that 21 of 37 plasma samples from rheumatoid arthritis patients had significantly elevated levels of C4d/C4 ratios. In addition, 8 of 21 RA patients with elevated C4d/C4 ratios were reported to have normal plasma levels of C4 antigen and total complement CH50 functional activity, J. F. Nitsche, Am. J. Clin. Path. 76:679–684 (1981).

Complement activation with concomitant C3a anaphylatoxin production in vivo has been demonstrated in patients undergoing cardiopulmonary bypass surgical procedures. Thus, plasma C3a levels were increased by greater than 5 fold in 15 of 15 adults during cardiopulmonary bypass surgery, D. E. Chenoweth, et al., New Engl. J. Med. 304:497–503 (1981). Both C4a and C3a anaphylatoxin levels were found to be elevated in plasma samples obtained immediately following protamine sulfate administration to heparinized patients, D. E. Chenoweth, Complement, 3:152–165 (1986). The anaphylatoxin levels Were quantitated in these studies by radioimmunoassay (RIA) procedures.

More recently, studies have also been reported which measured plasma C3 fragment levels in an effort to monitor C activation in patients with autoimmune diseases. Using a PEG precipitation procedure, W. J. W. Morrow, et al., concluded that plasma levels of C3d,g fragments varied in direct proportion with disease activity in 43 RA patients, W. J. W. Morrow, et al., Annal Rheumatic Dis. 42:668–671 (1983). A highly sensitive EIA test for the quantitation of C3d,g has been reported which measured elevated C3d,g levels in 12 of 22 patients with a variety of infectious and autoimmune diseases, T. E. Mollnes, Scand. J. Immunol. 21:607–613 (1985). And, a mouse monoclonal antibody reactive with a neoantigenic determinant present on iC3b, C3d,g and C3d fragments has been utilized to quantitate iC3b/C3d,g activation fragments in patient plasma specimens. Using this anti-iC3b/C3d,g neoantigen reactive monoclonal antibody in radiolabeled form, a competitive RIA procedure was developed which measured significantly increased iC3b/C3d,g fragment levels in 16 of 25 SLE and 5 of 12 RA patient plasma specimens, J. D. Tamerius, et al., J. Immunol. 135:2015–2019 (1985).

Several assay procedures have also been developed to measure terminal C component activation in patients. The report of Falk, et al. indicated elevated SC5b-9 complex levels in serum samples obtained from 13 of 14 patients with active SLE, R. F. Falk, et al., New Engl. J. Med. 312:1594–1599 (1985). These authors also reported the mean SC5b-9 complex concentration in SLE patients with active disease was 10 fold higher than the mean SC5b-9 concentration in SLE patients that were clinically stable. They further concluded that the SC5b-9 complex concentration in SLE patient serum samples was a more sensitive measure of disease activity than total C3 antigen, total C4 antigen, or total CH50 assay results. The assay used in this study to quantitate SC5b-9 complex levels was an RIA procedure employing a mouse monoclonal antibody reactive with an SC5b-9 complex specific neoantigenic determinant.

A quantitative EIA has also been developed to measure SC5b-9 complex levels in cerebrospinal fluids (CSF), M. E. Sanders, et al., J. Immunol. 136:4456–4459 (1986). Using this EIA procedure, CSF from 13 of 14 patients with acute Guillain-Barre Syndrome and 16 of 21 patients with multiple sclerosis had significantly elevated levels of SC5b-9 complex. A quantitative EIA has also been developed using polyclonal IgG fractions to measure SC5b-9 complex levels in a prospective study of SLE, M. S. Gawryl, et al., Arthritis Rheum. 31:188–195 (1988). SC5b-9 complex levels were determined in 11 patients with various manifestations of SLE for a two-year period during active and inactive phases of disease. In 9 of the 11 patients, elevations in SC5b-9 complex concentrations correlated with disease exacerbations. In many of these patients, C3 and C4 total antigen levels remained within normal concentration ranges during the study and were less sensitive indicators of disease activity than SC5b-9 complex concentrations, M. S. Gawryl, et al., Arthritis Rheum. 31:188–195 (1988).

Therefore, a new generation of tests has been developed to measure complement activation events in vivo in patients with a wide variety of diseases. The major driving force behind the development of these new tests has been the realization that the direct measurement of C activation fragments and/or complexes in patient plasma, serum or CSF specimens provides a much better measurement of C activation events and clinical disease activity in these patients than is possible from the older tests that measure total antigen levels. However, as tests to measure C activation become more specific and more highly sensitive, the collection, processing and storage of patient specimens becomes extremely critical because the spontaneous activation of C which occurs during storage in vitro must be prevented in order to avoid the creation of falsely elevated, i.e., positive, results. As discussed in detail above, the only procedure known currently that can prevent spontaneous C activation in vitro, is storage of the collected patient specimens at $-70°$ C. or below within 2–4 hours after collection, G. Garratty, Am. J. Clin. Path. 54:531–538 (1970); T. E. Mollnes, Scand. J. Immunol. 21:607–613 (1985); F. Hugo, J. Immunol. Meth. 99:243–251 (1987); P. F. Langlois and M. S. Gawryl, Fed. Proc. 46:772 (1987). In many research, hospital and clinical labs, it may be impossible to conduct the collection, processing and storage of patient specimens under such exacting conditions. Therefore, it is the intent of this invention to allow for the storage of whole blood, plasma or serum at $-20°$ C. to $22°$ C. for a minimum of 48 hours in a composition that will prevent completely the spontaneous in vitro activation of the complement system.

Methods Used to Preserve Protein Structure and Function Upon Storage In Vitro

1. General Approaches

It is well known that many protein preparations and fractions are unstable upon prolonged storage in vitro under a wide variety of different storage conditions. Improved storage stability can be achieved by increasing the overall total protein concentration in the system or by the addition of stabilizers and additives. For example, immunoglobulin preparations at protein concentrations less than 15 wt % are unstable and form insoluble precipitates upon storage in liquid aqueous solution. This immunoglobulin instability is increased with increased storage temperatures from $4°$ to $37°$ C. To improve immunoglobulin preparation storage stability, J. L. Lundblad, et al., U.S. Pat. No. 4,186,192, disclosed greatly improved in vitro storage stability of immunoglobulin solutions (2.5 to 18 wt %) upon addition of maltose to 5 to 15 wt % and glycine to approximately 0.1M R. C. Mace, et al., U.S. Pat. No. 3,057,781, disclosed that proteins in human blood plasma are rendered heat (incubation at $60°$ C. for as long as 10 hr) and agitation stable by the addition of heated invert sugar (2.5 to 5 wt %) containing minor proportions of levulinec acid (0.01 to 2.0 wt %).

The addition of exogenous protein carriers, e.g., albumin or gelatin, has also been used to stabilize protein preparations in solution. For example, Japanese patent 90514/1983 proposed the use of human serum albumin as a stabilizer for purified preparations of $\gamma$-interferon (IFN). T. Terano, U.S. Pat. No. 4,659,570, disclosed that addition of chemically modified gelatin, i.e., gelatin treated with diisocyanate to form urea bridges, to a final 3.5 wt % concentration, was able to prevent the loss of IFN-$\alpha$, IFN-$\beta$ and INF-$\gamma$ activity in solution upon freeze-drying or drying at $40°$ C. by radiofrequency induction heating.

Freezing as well as freeze-drying are other processes frequently used to increase the stability of protein preparations and fractions upon storage in vitro. Thus, C. M. Li Mutti, et al., U.S. Pat. No. 4,127,502, disclosed the addition of sugars, sugar alcohols and sugar amines to serum or serum-derived compositions before freeze-drying in order to obtain superior homogeneity after reconstitution. A. Diedrichsen, et al., U.S. Pat. No. 4,462,980, disclosed the incorporation of polyhydroxyl compounds into an aqueous solution of plasmin before lyophilization to prevent plasmin aggregation and to prolong in vitro storage life. H. Hayashi, et al., U.S. Pat. No. 4,457,916, disclosed that incorporation of a mixture of a nonionic surfactant and a specific sugar into an aqueous solution or powder containing Tumor Necrosis Factor (TNF) will allow for prolonged storage, freezing, thawing, heat-treatment and freeze-drying of TNF without loss of activity.

The mechanism(s) by which these protein and polyhydroxyl compound additives are able to stabilize protein solutions appears to be due to the ability of these stabilizing agents to prevent or inhibit autodigestive enzyme reactions, surface contact denaturation, dilution denaturation and solution or freeze-thaw aggregation reactions.

2. Complement

Purified C proteins are traditionally stored frozen at $-70°$ C. or below. Occasionally purified complement proteins may be freeze-dried in an effort to allow longer in vitro storage at $-20°$ C. to $4°$ C. Purified C proteins are not usually stored in the presence of exogenous protein carriers since the protein carrier can interfere with protein determinations and radiolabeling procedures. In addition, exogenous protein carriers frequently introduce exogenous proteases into the purified C preparations which can induce C component fragmentation and loss of activity during storage in vitro. Since many C proteins are very sensitive to fragmentation by proteases, chemical protease inhibitors, e.g., diisopropyl fluorophosphate (DFP), phenylmethylsulfonyl fluoride (PMSF), para-nitrophenyl p'-guanidinobenzoate (NPGB), epsilon amino-n-caproic acid (EACA) or benzamidine, are frequently added to purified C protein preparations to improve storage stability, C. Bolotin, et al., Biochem. 16:2008–2015 (1977), C. H. Hammer, et al., J. Biol. Chem. 256:3995–4006 (1981). For example, Hammer and coworkers store their highly purified human C4 preparations as a sterile solution at 4.C in phosphate buffered saline, pH 7.3, containing 10 mM EDTA, with 25 $\mu$M NPGB being added to this sterile solution of C4 every four weeks. Under these conditions, C4 has a functional half-life of 5 months. Alternatively, C4 can be stored frozen at $-70°$ C. in the presence of protease inhibitor-treated 5% purified human albumin, which increases the C4 storage half-life to 12 months, In: *The Complement System*, K. Rother and G. Till (eds), Springer-Verlag, Heidelberg, in press. Highly purified human C1q, C8 and C9 have been stored in the presence of 40% glycerol to improve storage properties at $-20°$ to $4°$ C, W. P. Kolb, et al., J. Immunol. 122:2103–2111 (1979).

Currently, the only procedure employed to store whole plasma or serum samples in vitro to maintain full activity of the C system is storage of these samples frozen at $-70°$ C. or below, G. Garratty, Am. J. Clin. Path. 54:531–538 (1970). It is generally believed that storage of C proteins at ultracold temperatures improves the stability of C3 and C4 components by preventing the spontaneous water hydrolysis of the internal thiol ester bond present in these proteins. Thus, if the internal thiol ester bonds remain intact, C3b-like C3, C3(H20), and C4b-like C4, C4(H₂O), are not produced. Therefore, upon thawing, spontaneous C activation does not occur as rapidly since C3(H20) and C4(H20) have not been produced during the −70° C. storage period. As described above, the preparation of plasma, using either divalent cation chelators (EDTA or citrate) or anticoagulants (heparin), will inhibit or retard spontaneous C activation in vitro. However, these procedures are able to retard the spontaneous activation of C in vitro for only 2-6 hours in plasma specimens stored at 4. to 22.C.

Therefore, the process by which the C system of proteins is rendered stable to prolonged storage in vitro is not dependent upon the prevention of protein denaturation in solution, surface contact-denaturation or the prevention of protein aggregation, as is the case with proteins in general as described above.

Rather, it would appear that the process by which the C system of proteins present in human plasma samples would be rendered stable to prolonged storage in vitro would be dependent upon the prevention or inhibition of the spontaneous hydration reaction and scission of the C3 and C4 α-chain internal thiol ester bonds. Therefore, the ability of the present invention to prevent the spontaneous activation of the C system in mammalian whole blood, plasma or serum under a variety of in vitro storage conditions, could not have been predicted to be effective based upon prior art knowledge in the field of C research. The mechanism by which the present invention is able to prevent the spontaneous activation of C upon in vitro storage is currently unknown.

SUMMARY OF THE INVENTION

In accordance with the present invention, a method for treating complement-containing samples is disclosed which prevents the spontaneous activation of complement in such samples.

Use of the method avoids the need to store complement-containing samples at temperatures at or below −70° C. while awaiting assays. When an effective concentration of a complement activation preventive saccharide is added to such samples, they may be held at conventional storage temperatures, that is stored frozen at −1° C. to −20° C. or stored in liquid form refrigerated at +1° C. to +14° C. or in liquid form at room temperature (15° C. to 30° C.) for a convenient period of time and at least 48 hr preliminary to assays, without causing erroneous assay results. The prevention of complement activation in turn prevents the production and release of complement activation fragments and complexes, comprising C4d, iC3b, C3d,g, Bb and the SC5b-9 complex as well as C4a, C3a, C5a and Ba fragments.

According to the object of the invention, we have found that many polyhydroxyl compounds are effective in preventing the spontaneous activation of complement in complement-containing samples during in vitro storage, including members of the classes of monosaccharides, disaccharides and oligosaccharides, as well as their amino and alcohol derivatives. Such saccharides comprise D-glucose (both the α and β anomers as well as a mixture containing any possible proportion of the α and β anomers), sucrose, D-ribose, gentiobiose, melibiose and trehalose. In a particularly preferred embodiment, the complement-activation preventive saccharide is β-D-glucose.

In one embodiment of the invention an effective amount of a divalent cation chelator is also added to the complement-containing samples. In a preferred embodiment, the divalent cation chelator is ethylene diamine tetraacetic acid (EDTA).

In yet another embodiment of the invention, the method also provides the addition of an effective amount of an anti-coagulant to the complement-containing samples. In a preferred embodiment, the anti-coagulant is heparin. In a particularly preferred embodiment, the invention provides a mixture of a complement activation-preventive monosaccharide, disaccharide or oligosaccharide, or an amino or alcohol derivative of one of these saccharides, together with a divalent cation chelator and an anti-coagulant. In yet another embodiment of the invention, this mixture is present within an evacuated chamber or vial, such as a Vacutainer ™ into which blood samples are drawn for collection.

According to another aspect of the invention there is provided a method for selecting a polyhydroxyl compound comprising a monosaccharide, disaccharide or oligosaccharide species or amine or alcohol derivative thereof for use in preventing the activation of complement in a complement-containing sample and determining the effective amount of the compound, comprising: providing a series of solutions of each species to be considered, the series having a range of concentrations; adding a quantity of each of said solutions to separate aliquots of a standard complement-containing sample in identical ratios of approximately 1:1; storing the mixtures of standard samples and solutions under selected conditions for selected periods of time; assaying the stored samples to determine the presence and concentration of fragments of complement proteins known to be produced as a consequence of complement activation; comparing the determined levels of complement protein fragments in the treated sample with the corresponding levels of complement protein fragments in control samples; and selecting the species and the concentration of the species corresponding to the solution in which the activation of complement was shown to be minimal and within a defined acceptable range.

According to yet another aspect of the invention, there is provided a composition for preventing the spontaneous activation of complement in a sample, comprising an effective complement activation-preventive amount of a polyhydroxyl compound, comprising a monosaccharide, disaccharide, oligosaccharide, or amine or alcohol derivative thereof, or a mixture thereof together with a divalent cation chelator and an anti-coagulant.

The invention also provides a complement-containing sample having added thereto an effective complement activation-preventive amount of a polyhydroxyl compound, comprising a monosaccharide, disaccharide or oligosaccharide or an amino or alcohol derivative of one of these saccharides. In a preferred embodiment, there is provided a complement-containing sample containing an effective complement activation-preventive amount of β-D-glucose.

According to yet another embodiment of the invention there is provided a method for determining the concentration of a complement protein or a complement protein physiological fragment thereof present in a complement-containing sample, comprising the steps of adding an effective complement activation-preventive amount of a polyhydroxyl compound comprising a monosaccharide, disaccharide or oligosaccharide or an amino or alcohol derivative of one of these or a mixture thereof to the complement-containing sample and then assaying the complement-containing samples to determine the concentration of a complement protein or a complement protein physiological fragment thereof by means of an appropriate specific procedure. In a preferred embodiment, the additional step of this method includes the addition of an effective amount of divalent cation chelator. In a particularly preferred embodiment, the method includes the step of storing the sample at a temperature of 4° to 10° C. for a period not exceeding seven days prior to the assay step.

In yet another embodiment of the invention the complement activation-preventive method is used in conjunction with the determination of a complement protein or a complement protein physiological fragment thereof as determined by an immunoassay procedure. In a particularly preferred embodiment, the complement protein or the complement protein physiological fragment is determined by enzyme immunoassay.

In yet another embodiment of the invention, there is provided a kit for determining the concentration of a complement protein or complement protein physiological fragment thereof in a complement-containing sample, comprising reagents to prevent the spontaneous activation of complement, comprising an effective quantity of a complement activation-preventive monosaccharide, disaccharide or oligosaccharide or an amino or alcohol derivative of one of these saccharides together with reagents and materials required for the determination of a specific complement protein or complement protein physiological fragment thereof in said complement-containing sample.

In a particularly preferred embodiment, the kit comprises a mixture containing an effective quantity of a complement activation-preventive monosaccharide together with an effective amount of divalent cation chelator and an anti-coagulant together with reagents and materials required for the enzyme immunoassay determination of a specific complement protein or complement protein physiological fragment thereof in a complement-containing sample.

According to yet another aspect of the invention, there is provided a method for preventing the spontaneous activation of coagulation in vitro in a sample containing at least one member of the coagulation system of proteins, comprising adding to the sample an effective activation-preventive amount of a monosaccharide, disaccharide or oligosaccharide or an amine or alcohol derivative thereof, or mixture thereof. In a preferred embodiment, the sample comprises blood or a fraction thereof.

These and other advantages and features of the present invention will become more fully apparent from the following description and appended claims.

BRIEF DESCRIPTION OF THE DRAWINGS

FIG. 13. The effect of sodium heparin on preventing spontaneous C4 activation in EDTA normal human plasma as determined by using the C4d fragment EIA.

FIGS. 14A and 14B. The ability of various polyhydroxyl compounds to protect EDTA normal human plasma samples against spontaneous complement activation. FIG. 14A: Complement activation as determined by C4d EIA and iC3b EIA. FIG. 14B: Complement activation as determined by C3d, g iC3b EIA, Bb EIA, and Raji CIC EIA.

FIGS. 15A and 15B. A comparative summary of the ability of various classes of polyhydroxyl compounds to inhibit spontaneous complement activation in EDTA normal human plasma samples stored in vitro at 22° C., for 48 hours. FIG. 15A: pentose, hexose, hexosamines, hexose alcohols, and cyclohexanehexol classes. FIG. 15B: ketoheptose, disaccharide, trisaccharide, polysaccharide and nonionic surfactant classes.

FIG. 16. Measurement of spontaneous C4 activation as a function of time in EDTA or heparin whole blood and plasma samples stored in vitro on ice or at 22° C., as determined by using the C4d fragment EIA.

FIG. 17. Measurement of spontaneous C3 activation as a function of time in EDTA or heparin whole blood and plasma samples stored in vitro at various temperatures, as determined by using the C3 activation fragment assays.

FIG. 18. Measurement of spontaneous Factor B activation as a function of time in EDTA-NHP stored at various temperatures, as determined by using the Bb fragment EIA.

FIG. 19. Measurement of spontaneous complement activation in various complement-containing samples treated with PBS or Solution B, as determined by various complement activation fragment assays.

FIG. 20. Effect of pre-dilution of samples on spontaneous complement activation in untreated complement-containing samples and those treated with Solution B, as determined by C4d and C3d,g/iC3b complement activation fragment assays.

FIG. 21. Summary of the minimum time periods which untreated samples can be stored at various temperatures before spontaneous complement activation becomes detectable, as determined by various complement activation fragment assays.

FIG. 22. Summary of the minimum time periods which samples treated with Solution B can be stored at various temperatures before spontaneous complement activation becomes detectable, as measured by various complement activation fragment assays.

DETAILED DESCRIPTION OF THE INVENTION

Figure 1:
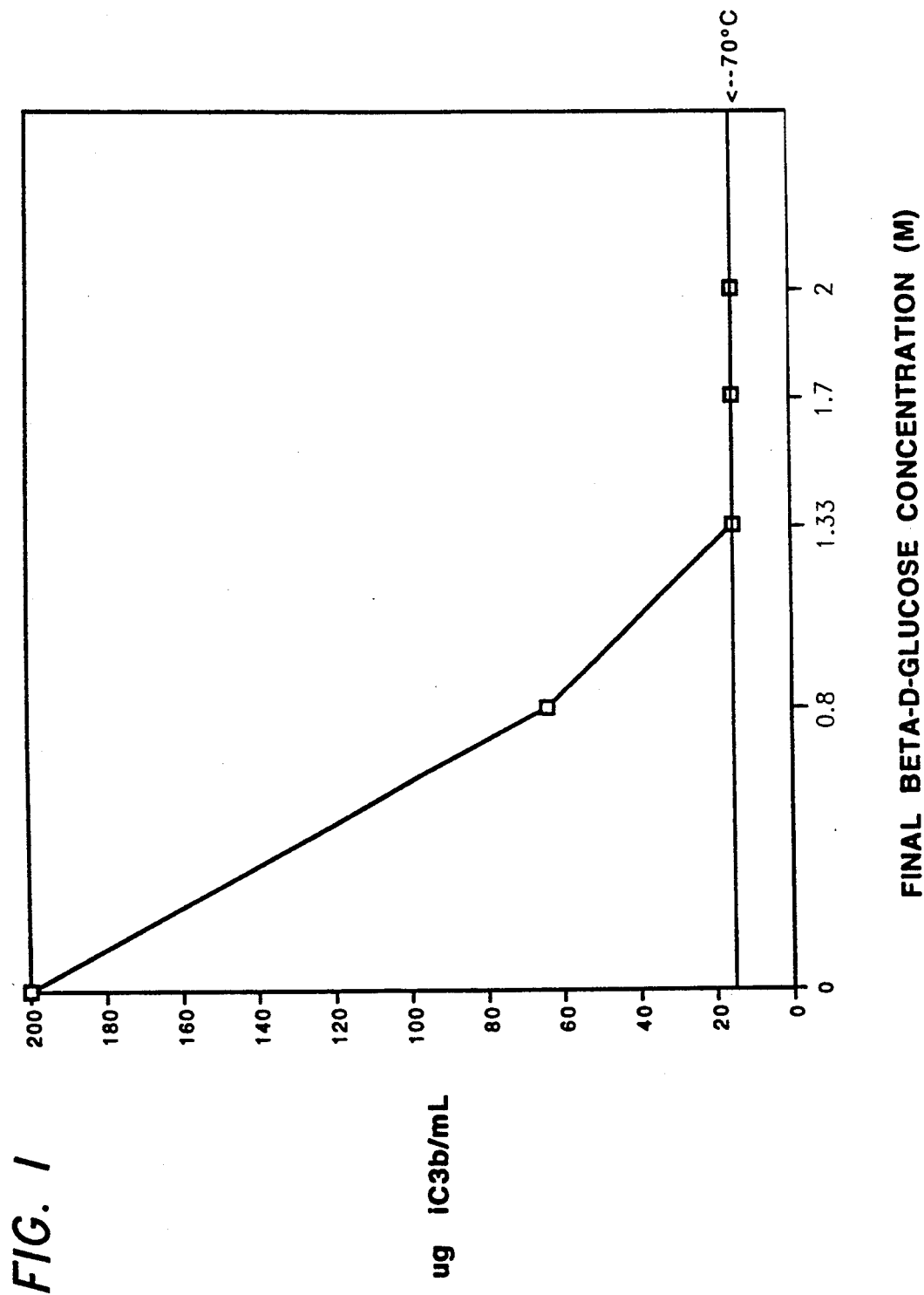
FIG. 1. Protective effects of $\beta$-D-glucose on human complement. 250 $\mu$L of freshly drawn EDTA-normal human plasma (EDTA-NHP) was mixed with 0 to 250 $\mu$L of 4M $\beta$-D-glucose dissolved in deionized water. All reaction mixtures were brought up to a final reaction volume of 500 $\mu$L using deionized water as the diluent. Each reaction mixture was mixed thoroughly, incubated at 22° C. for 48 hr and assayed for iC3b fragment levels. A non-incubated control (−70° C.) was prepared by mixing 1 part EDTA-NHP with 1 part 4M $\beta$-D-glucose dissolved in deionized water. This control reaction mixture was stored at −70° C. until it was assayed in the iC3b fragment EIA along with the incubated experimental samples.
Figure 2:
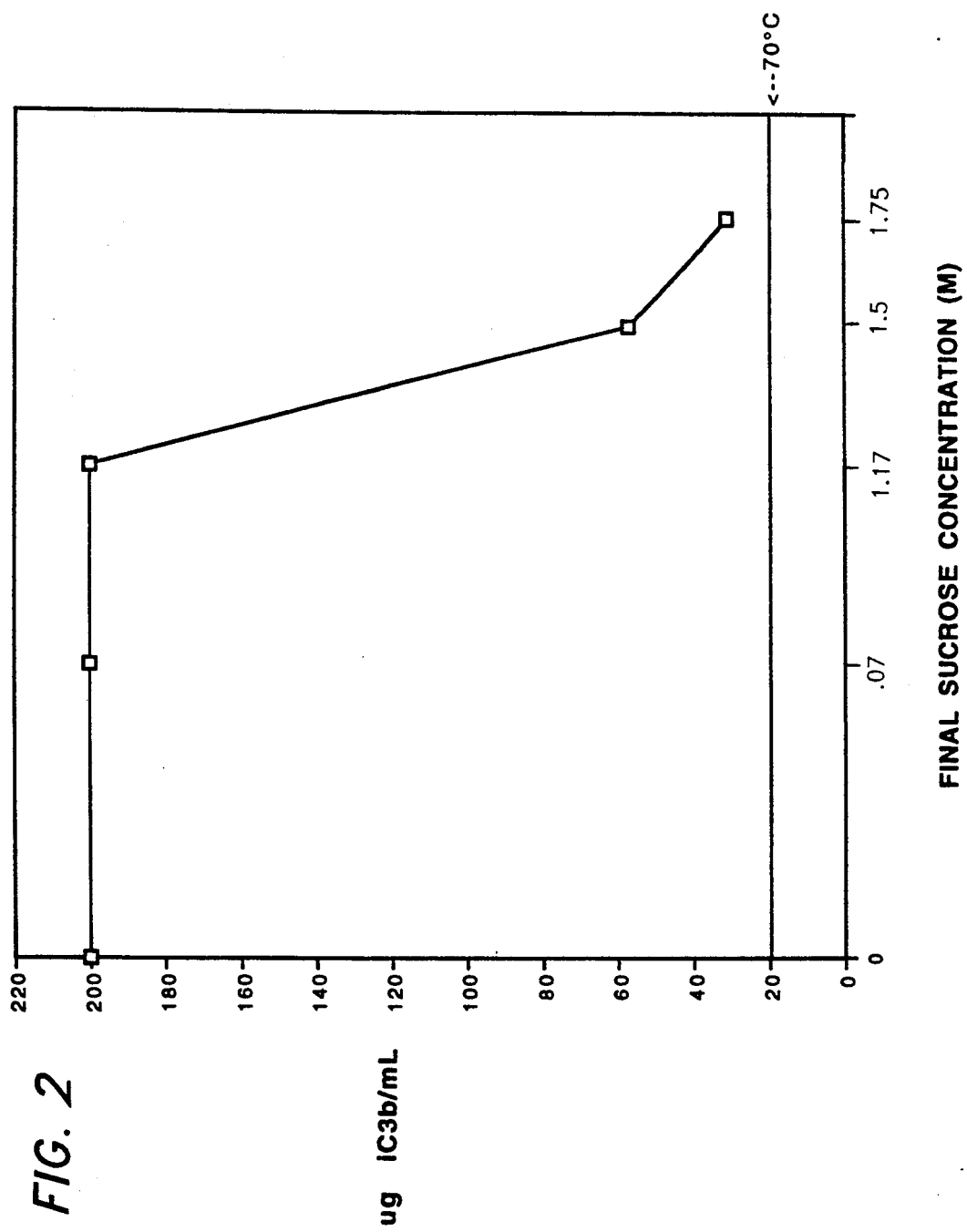
FIG. 2. Protective effects of sucrose on human complement. Freshly drawn EDTA-NHP was incubated at 22° C. for 48 hr with increasing concentrations of sucrose, using a 3.5M sucrose stock solution prepared in deionized water, as described in the legend to FIG. 1. The experimental incubation mixtures and the non-incubated −70° C. control were assayed for iC3b fragment levels using the iC3b fragment EIA.
Figure 3:
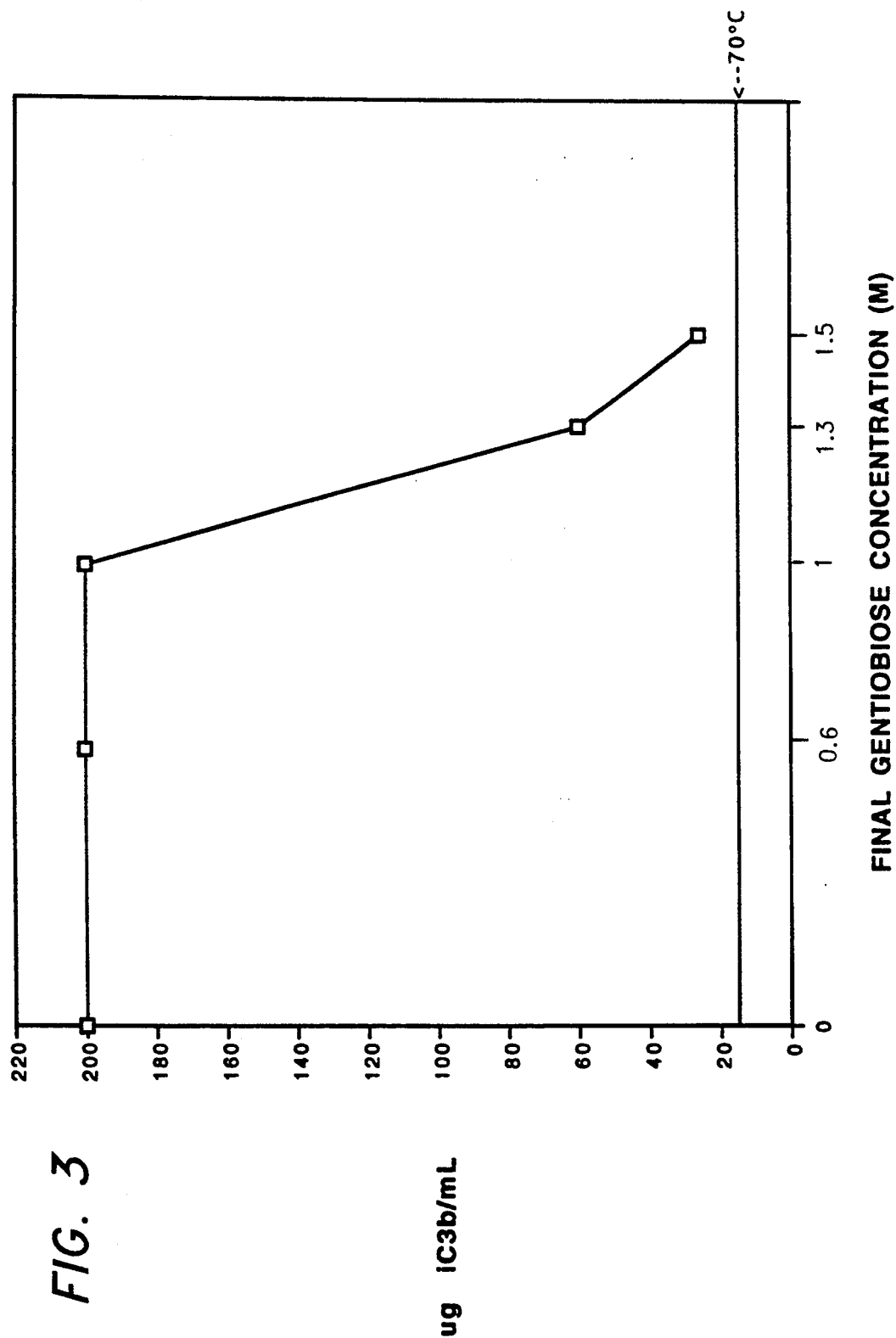
FIG. 3. Protective effects of gentiobiose on human complement. Freshly drawn EDTA-NHP was incubated at 22.C for 48 hr with increasing concentrations of gentiobiose, using a 3M gentiobiose stock solution prepared in deionized water, as described in the legend to FIG. 1. The experimental incubation mixtures and the non-incubated −70° C. control were assayed for iC3b fragment levels using the iC3b fragment EIA.
Figure 4:
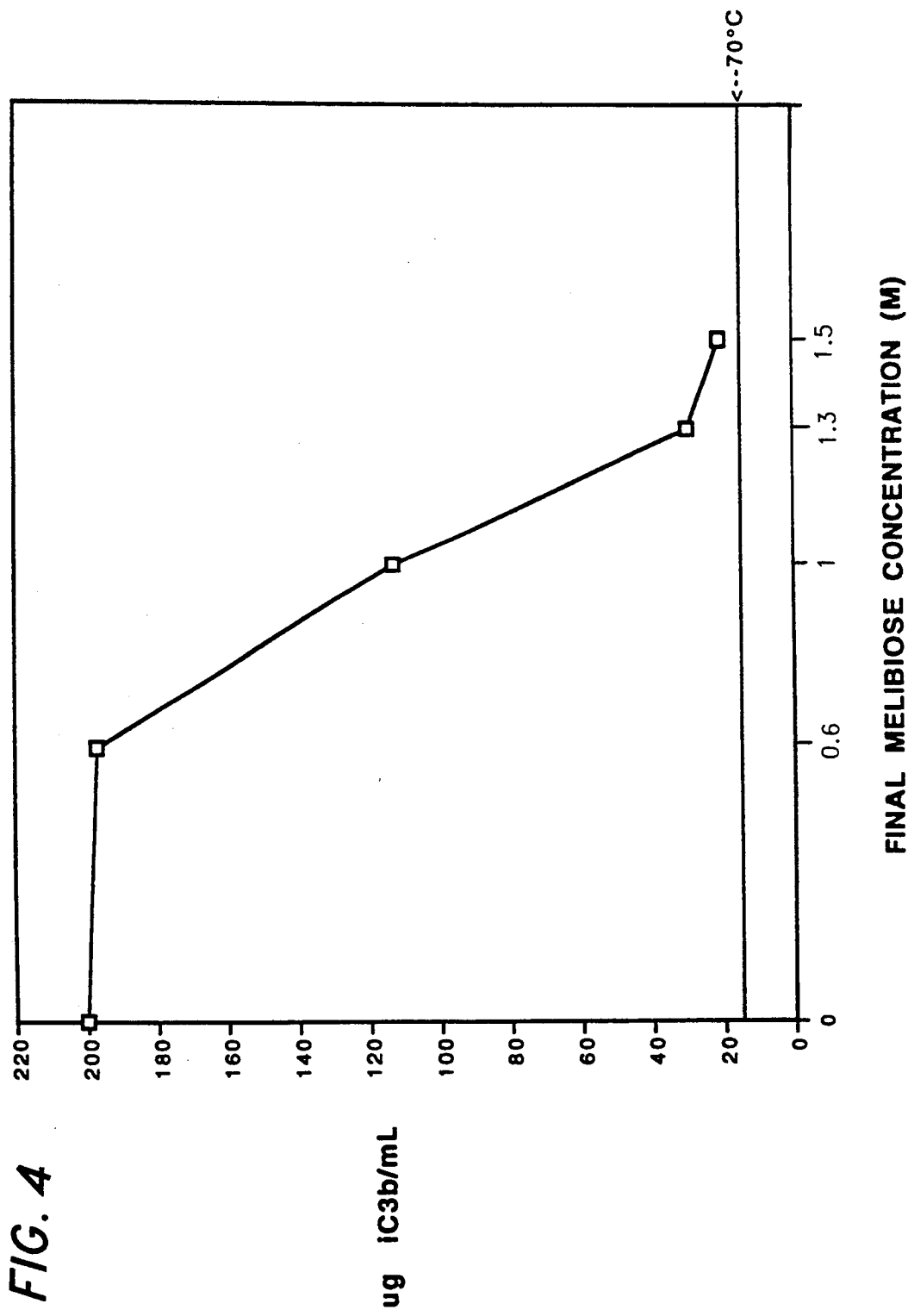
FIG. 4. Protective effects of melibiose on human complement. Freshly drawn EDTA-NHP was incubated at 22° C. for 48 hr with increasing concentrations of melibiose, using a 3M melibiose stock solution prepared in deionized water, as described in the legend to FIG. 1. The experimental incubation mixtures and the non-incubated −70° C. control were assayed for iC3b fragment levels using the iC3b fragment EIA.
Figure 5:
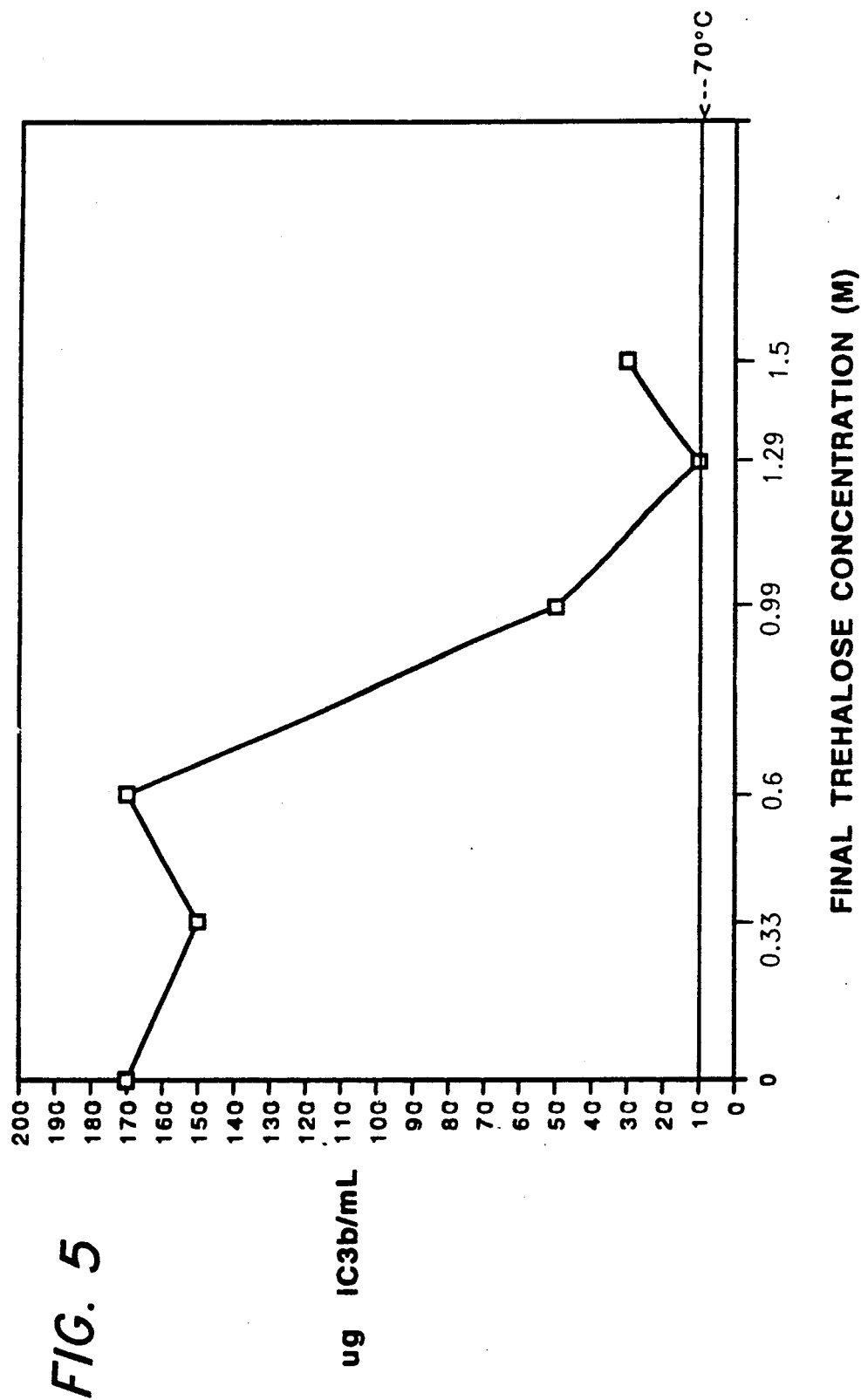
FIG. 5. Protective effects of trehalose on human complement. Freshly drawn EDTA-NHP was incubated at 22° C. for 48 hr with increasing concentrations of trehalose as described in the legend to FIG. 1. The experimental incubation mixtures and the non-incubated −70° C. control were assayed for iC3b fragment levels using the iC3b fragment EIA.

Selected polyhydroxyl compounds are found to be effective in preventing the spontaneous activation of complement in complement-containing samples for extended periods of time when the compounds are added to such samples in effective concentrations.

In this context, complement-containing samples are defined as whole blood, whole or fractionated plasma, and whole or fractionated serum obtained from normal human donors or from human patients. Complement-containing samples are also defined as whole blood, whole or fractionated plasma and whole or fractionated serum obtained from normal, abnormal or experimental mammals. Complement-containing samples are further defined as any fluid obtained from a mammal which contains complement, e.g., synovial fluids, cerebrospinal fluids, pleural fluids, ascites fluids, ocular fluids and tissue or organ lavage fluids.

The complement activation processes which the polyhydroxyl compounds of this invention prevent are exemplified by the enzymatic conversion or degradation of C4 to C4a and C4b fragments; C4b to C4c and C4d fragments; C3 to C3a and C3b fragments; C3b to iC3b and C3f fragments; iC3b to C3c and C3d,g fragments; C5 to C5a and C5b fragments, the formation of which can result in SC5b-9 complex assembly; and Factor B to Ba and Bb fragments.

A method for screening compounds to determine the complement preventing effectiveness thereof is described in detail in the course of the following experimental description and discussion. The method essentially comprises treating complement-containing samples with various doses of the test compounds, storing the thus-treated sample at conventional storage temperature for a minimum of about 48 hours and determining the extent of complement activation which occurs during the storage period by performing assays on the sample for various complement activation products. The results are compared with determination of the level of the same activation products at the beginning of the storage period, i.e., a non-incubated control sample. A non-treated control, comprising an identical sample diluted with phosphate buffered saline (PBS) in a volume ratio identical to that of the sample and polyhydroxyl solution is similarly assayed.

Assays used to test for the occurrence of complement activation comprise those for C4d, iC3b, C3d,g, Bb and SC5b-9 complex; however, since C4a, C3a, C5a and Ba fragments are produced concomitantly in the activation process, suppression of levels of the fragments assayed implies suppression of levels of those in the latter group also.

COMPOSITION OF INVENTION COMPONENTS

Several experiments were conducted to determine which polyhydroxyl compounds might have the ability to inhibit the spontaneous activation of C in normal human ethylenediamine tetraacetic acid (EDTA) plasma samples (EDTA-NHP) stored in vitro. Several different polyhydroxyl compounds were individually dissolved in deionized water to obtain solutions of each compound at a concentration approaching saturation at 22° C. Freshly drawn EDTA-NHP was mixed with increasing concentrations of the polyhydroxyl compound to be tested keeping the final reaction volumes constant. For example, 250 µL of freshly drawn EDTA-NHP was mixed with 0 to 250 µL of the concentrated polyhydroxyl solution to be tested. All reaction mixtures were brought up to a final reaction volume of 500 µL using deionized water as the diluent. Each reaction mixture was mixed thoroughly and incubated at 22° C. for 48 hr. A non-incubated control was prepared for each experiment by mixing 1 part EDTA-NHP with 1 part of the concentrated polyhydroxyl solution to be tested. This control mixture was held at −70° C. until it was thawed out, along with the other experimental samples, and assayed for the occurrence of spontaneous complement activation. For this initial set of experiments, iC3b fragment levels were quantitated in all test samples using the Cytotech monoclonal antibody based EIA procedure. The first analyte selected to be measured was iC3b since, based on previously published data as outlined above, it was anticipated that the C3 protein would be the most susceptible to spontaneous activation upon storage of EDTA-NHP in vitro. The results presented in FIGS. 1, 2, 3, 4 and 5 demonstrate the protective effects of $\beta$-D-glucose, sucrose, gentiobiose, melibiose and trehalose on human complement, at least as measured by the prevention of spontaneous C3 activation in EDTA-NHP samples stored in vitro at 22° C. for 48 hr. In all cases, spontaneous iC3b fragment production was inhibited with increasing concentrations of each polyhydroxyl compound present in the EDTA-NHP samples. In this regard, $\beta$-D-glucose and trehalose, when present at final concentrations equal to or greater than 1.3M, completely prevented spontaneous iC3b fragment production. This conclusion was determined by comparing the iC3b concentration present in the untreated −70° C. control with the results obtained from the experimental sample incubation mixtures.

Figure 6:
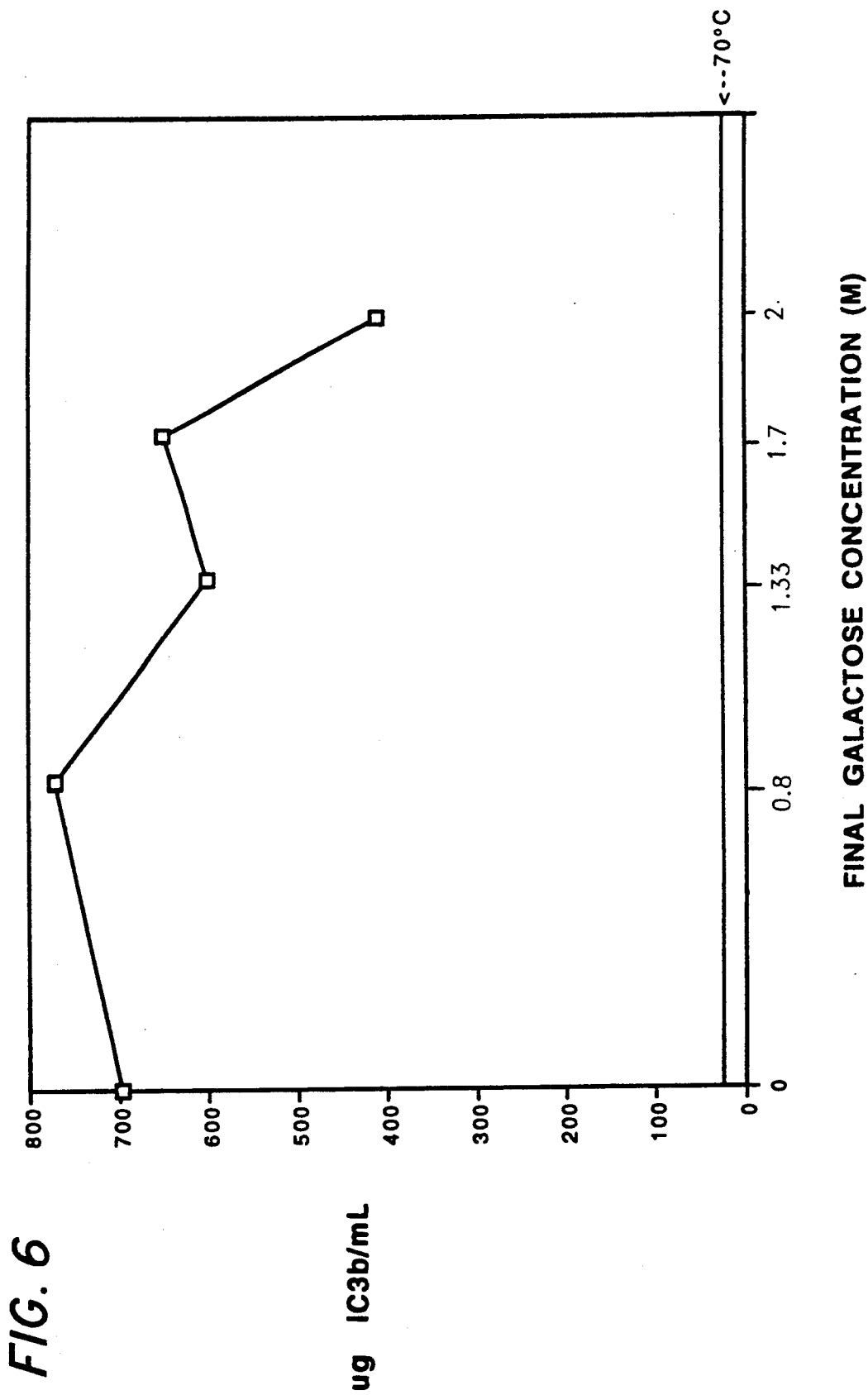
FIG. 6. Lack of protective effects of galactose on human complement. Freshly drawn EDTA-NHP was incubated at 22° C. for 48 hr with increasing concentrations of galactose as described in the legend to FIG. 1. The experimental incubation mixtures and the non-incubated −70° C. control were assayed for iC3b fragment levels using the iC3b fragment EIA.
Figure 7:
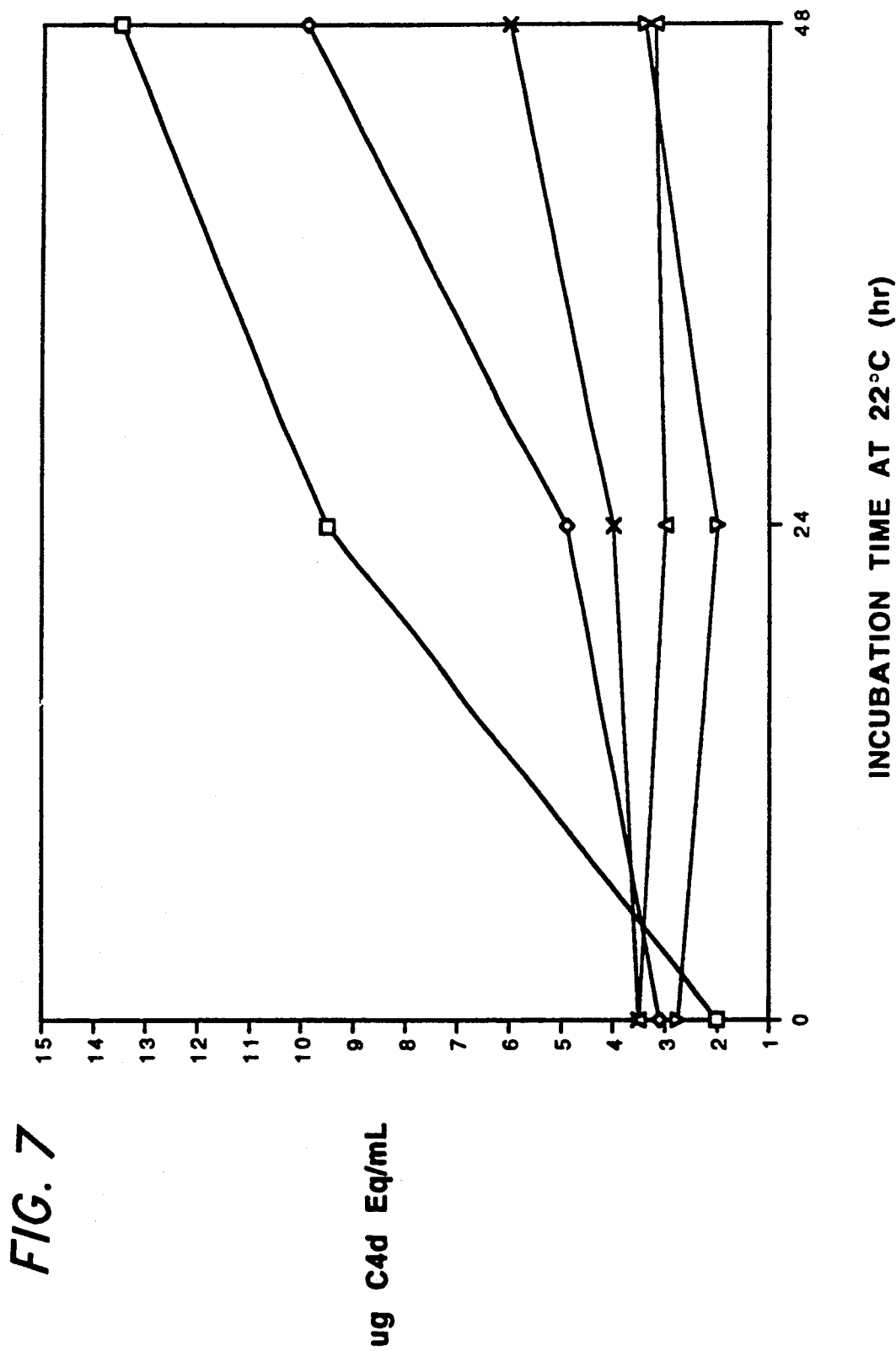
FIG. 7. Prevention of spontaneous C4 activation in normal human plasma collected in EDTA, citrate or heparin anticoagulants. Normal human plasma was prepared from blood collected into vacutainer TM tubes containing sodium EDTA, sodium citrate or sodium heparin as the anticoagulant. Each freshly prepared plasma sample was mixed with an equal volume of either PBS (phosphate buffered saline) or Solution B (4M $\beta$-D-glucose, 40mM EDTA and 30 IU sodium heparin/mL, pH 7.2±0.2) and stored at 22° C. After the storage time periods indicated, samples were collected and stored at −70° C. The collected samples were thawed all at once and spontaneous C4 activation was quantitated using the C4d fragment EIA. The results are shown as $\mu$g C4d equivalents/mL present in each experimental plasma sample as a function of time. Plasma incubation conditions: EDTA-NHP mixed with PBS (open square symbols); EDTA-NHP mixed with Solution B (plus (+) symbols); sodium citrate plasma mixed with PBS (X symbols); sodium citrate plasma mixed with Solution B (inverted open triangle symbols); sodium heparin plasma mixed with PBS (open diamond symbols); sodium heparin plasma mixed with Solution B (open triangle symbols).

Not all polyhydroxyl compounds tested were able to inhibit the spontaneous activation of C3. Thus, as shown in FIG. 6, when freshly drawn EDTA-NHP was incubated at 22° C. for 48 hr with increasing final concentrations of galactose (a final galactose concentration of 2M was the highest concentration studied), only slight inhibition of spontaneous iC3b fragment production was observed.

As discussed in detail above, both the classical and alternative complement activation pathways have divalent cation requiring reaction steps. Thus, EDTA is routinely added to plasma or serum specimens to inhibit the activation of both C pathways, N. R. Cooper, et al., In: *Immunological Diseases*, M. Samter (ed), Little Brown and Co., Boston, Massachusetts (1971), pp. 289-331; M. K. Pangburn and H. J. Muller-Eberhard, Springer Semin. Immunopath. 7:163-192 (1984). The divalent cation $Ca^{++}$ is also required for activation of both the intrinsic and extrinsic pathways of the coagulation cascade of blood plasma. Therefore, EDTA is also a potent inhibitor of fibrin clot formation. Since the current invention was designed to prevent the spontaneous activation of the C system in serum, as well as in a variety of different plasma samples, a preferred embodiment of the invention contains the divalent cation chelator EDTA. EDTA, when added to whole blood, or when present in plasma at a final concentration of 1 mM or greater, will inhibit activation of the coagulation system and fibrin clot formation; and when added to plasma or serum to a final concentration of 1 mM or greater, EDTA will also inhibit activation of the complement system. Therefore, the preferred embodiment of the invention will provide a concentration of EDTA to the complement-containing sample equal to or greater than 1 mM.

FIG. 13 presents the C4d fragment EIA results obtained from a representative experiment in which EDTA-NHP was mixed with an equal volume of Stabilizing Solution containing 0 to 60 IU sodium heparin/mL. In this experiment the Stabilizing Solution diluent consisted of 4M $\beta$-D-glucose and 40 mM EDTA dissolved in deionized water, pH 7.2. The sample mixtures were incubated at 22.C for the time periods indicated, samples were collected and immediately stored at −70° C. A non-incubated control was prepared by mixing 1 part EDTA-NHP with 1 part Stabilizing Solution containing no heparin. The non-incubated control mixture was stored at −70° C. until assayed in the C4d fragment EIA along with the incubated experimental samples. The non-incubated EDTA-NHP control in this experiment contained 1.1 μg C4d Eq/mL. A set of non-treated controls were also prepared and incubated at 22° C. for the time periods indicated by mixing EDTA-NHP with an equal volume of PBS. The data from this experiment indicated that addition of 15 to 30 IU sodium heparin/mL to a solution of 4M β-D-glucose and 40 mM EDTA provided the maximum protection against spontaneous C4 activation in EDTA-NHP incubated at 22° C. It is of interest to note that when compared to the results obtained with the non-treated PBS control, 4M β-D-glucose and 40 mM EDTA, even without addition of any sodium heparin, provided considerable protection against the occurrence of spontaneous C4 activation during the in vitro storage periods tested. However, by comparing the C4d fragment levels in EDTA-NHP samples incubated at 22° C. for 72 hr in the presence of Stabilizing Solution with 0 or 15 to 30 IU sodium heparin/mL, it is clear that β-D-glucose and EDTA alone were not able to prevent completely the spontaneous activation of C4 in these samples. Therefore, the preferred embodiment of the present invention does include the addition of 15 to 30 IU of sodium heparin/mL in order to provide for the maximum protection against spontaneous C4 activation in a complement-containing sample during storage in vitro. In this regard, the beneficial effects of sodium heparin as a preventative of spontaneous C activation can only be demonstrated consistently with the inhibition of spontaneous C4 fragment production. Therefore, the presence of sodium heparin does not improve the storage behavior of C3, Factor B, or the terminal complement proteins.

An extensive series of experiments were conducted to examine the ability of a large variety of polyhydroxyl compounds to prevent the spontaneous activation of C in EDTA-NHP during in vitro storage at 22° C for 48 hr. EDTA-NHP was mixed with an equal volume of Buffer B containing the polyhydroxyl compound to be tested. In these experiments Buffer B consisted of 40 mM EDTA and 30 IU sodium heparin/mL dissolved in deionized water, pH 7.2. The final concentration of polyhydroxyl compound dissolved in Buffer B varied for each compound due to differences in solubility. For each set of experiments, EDTA-NHP was also diluted and mixed with an equal volume of PBS (untreated control). The EDTA-NHP samples mixed with each polyhydroxyl compound dissolved in Buffer B and the corresponding untreated controls were incubated at 22° C. for 48 hr, stored at −70° C. and subsequently assayed for C4d, iC3b, C3d,g/iC3b and Bb complement fragment levels as well as for circulating immune complex levels using the Raji Cell Replacement EIA. The results from this study, presented in FIG. 14, indicated that the various polyhydroxyl compounds differed greatly in their ability to protect against spontaneous C activation in EDTA-NHP stored in vitro at 22° C. for 48 hr. For example, β-D-glucose dissolved in Buffer B and mixed with an equal volume of EDTA-NHP to a final β-D-glucose concentration of 2M, completely prevented the spontaneous activation of C3 while final concentrations of 1.5M D-raffinose, 2M D-mannosamine, 1.5M D-mannitol, 0.5M inositol, 0.5M glucosamine and 2M galactose were ineffective at preventing the spontaneous activation of C3 in these complement-containing samples. This conclusion was based upon the iC3b percent protection values determined for each of the polyhydroxyl compounds (treated samples) as listed in FIG. 14.

The data presented in FIG. 14 also indicated that many polyhydroxyl compounds demonstrated differential protective effects for the different analytes studied. For example, β-D-glucose dissolved in Buffer B and mixed with an equal volume of EDTA-NHP to a final β-D-glucose concentration of 2M, completely prevented the spontaneous activation of C4 (as measured by C4d fragment production), C3 (as measured by iC3b and C3d,g/iC3b fragment production) and Factor B (as measured by Bb fragment production) while 2-deoxy-D-ribose at a final concentration of 2M was able to prevent the spontaneous activation of C4 but was ineffective at preventing the spontaneous activation of C3. In contrast, D-mannitol and D-raffinose, dissolved in Buffer B and mixed with an equal volume of EDTA-NHP to a final D-mannitol or D-raffinose concentration of 1.5M, were unable to inhibit the spontaneous activation of C4 or C3 in the EDTA-NHP sample stored at 22° C. for 48 hours.

In general, Factor B present in EDTA-NHP appeared to be the least susceptible to spontaneous activation under the storage conditions studied, irrespective of the polyhydroxyl compound employed. In addition, Factor B appeared to be relatively stable in the untreated samples as well. This can be seen by comparing the Bb fragment percent protection values with the other analyte percent protection values determined for the EDTA-NHP samples incubated at 22° C for 48 hr after mixing with an equal volume of PBS alone. In comparison, C3 present in EDTA-NHP appeared to be the most susceptible to spontaneous activation under the storage conditions studied. This can be seen from the data presented in FIG. 14 by comparing the iC3b and C3d,g/iC3b fragment percent protection values with the other analyte percent protection values determined for the EDTA-NHP samples incubated at 22.C for 48 hr after mixing with an equal volume of the various polyhydroxyl compounds in Buffer B or PBS.

The various polyhydroxyl compounds tested in FIG. 14 were also tested for their ability to prevent spontaneous C activation in EDTA-NHP during in vitro storage at 4.C for 48 hr. The results were similar to those presented in FIG. 14 except that the extent of spontaneous C activation observed was significantly less in all samples due to the lower temperature of storage (data not shown).

Each polyhydroxyl compound tested in the invention (as seen in FIG. 14) is listed in FIG. 15 according to its general biochemical classification. Also shown in FIG. 15 is the overall effectiveness of each polyhydroxyl compound to inhibit the spontaneous activation of C in a complement-containing sample stored at 22° C. for 48 hr.

The concentrations, expressed as μg analyte/mL, of a number of different activation products of spontaneous complement activation were measured in the course of these experiments. In an effort to normalize the data obtained from the various determinations so that the results from different assays could be directly compared to one another, a percent protection value was calculated for each analyte measured. The precent protection values were calculated by dividing the μg analyte/mL in the non-incubated, time-zero control sample by the μg analyte/mL in the experimental sample, multiplied by 100%. A percent protection value of 70 to 130% for any given analyte measured in an experimental sample was considered to indicate that the invention formulation tested was fully effective at providing protection against the occurrence of spontaneous complement activation. Ideally, the effective composition formulation would provide full protection against the occurrence of spontaneous complement activation in a complement-containing sample for all of the analytes measured. In fact, this was the case with several polyhydroxyl compounds when they were present in sufficiently high concentrations in a preferred embodiment of the invention.

The overall protective effectiveness of each polyhydroxyl compound was determined from the results presented in FIG. 14 by calculating the mean percent protection values observed for the C4d, iC3b and C3d,g/iC3b fragment EIAs. If the percent protection values for all three fragments were not available, the iC3b percent protection value alone was used. An A value was assigned if the mean percent protection was equal to or greater than 70%. A value of B was assigned if the mean percent protection was equal to or greater than 40% but less than 70%. A value of C was assigned if the mean percent protection was less than 40%.

A percent protection value range of 70 to 130% was used as a criterion to define that a given invention embodiment was able to provide full protection against spontaneous complement activation for the following reasons: The coefficient of variation for the EIA kits employed in these studies ranged from 10-30% when analyte levels were measured in the very low range of values found in freshly-drawn normal human plasma samples. Therefore, in order to ensure that a given result fell within the variability range of the assays employed, a percent protection value between 70 and 130% was considered to represent a fully protective effect. In actual practice, as seen in FIGS. 1 through 5 and 7 through 10, as well as in FIGS. 14 and 19, preferred embodiments of the invention were routinely able to provide percent protection values ranging from 85 to 115% for all the analytes studied when normal human plasma samples were pre-mixed with the preferred invention formulations and stored in vitro at −20° C. to 22° C. for as long as 7 days.

Based on the data presented in FIGS. 1 through 6 and FIGS. 13 through 15, many polyhydroxyl compounds were found to be effective in preventing the spontaneous activation of C in complement-containing samples during in vitro storage.

Different polyhydroxyl compounds which proved to be effective in the invention had different minimum final concentrations which provided protection. In general, if a polyhydroxyl compound, when used in a preferred invention formulation, had the ability to provide protection against spontaneous complement activation in a complement-containing sample during in vitro storage, a minimum final polyhydroxyl concentration of 0.5 to 1M was required in order to obtain reproducible, significant protective effects.

Specifically, the following ranges of final concentrations for each effective polyhydroxyl compound were found to provide protection against spontaneous complement activation in complement-containing samples during in vitro storage: 1) $\beta$-D-glucose, 0.5–4M; 2) sucrose, 1.2–4M; 3) gentiobiose, 1.0–4M; 4) melibiose, 0.6–4M; and 5) trehalose, 0.6–3.5M. The upper range of polyhydroxyl compound concentrations studied, i.e., 3.5–4.0M final concentrations, approached total saturation of an aqueous solution in all cases.

The following polyhydroxyl compounds were identified as particularly effective: (1) $\beta$-D-glucose when added to a complement-containing sample to a final concentration equal to or greater than 1.33M; (2) sucrose when added to a complement-containing sample to a final concentration equal to or greater than 1.75M; (3) gentiobiose when added to a complement-containing sample to a final concentration equal to or greater than 1.5M; (4) melibiose when added to a complement-containing sample to a final concentration equal to or greater than 1.5M; and (5) trehalose when added to a complement-containing sample to a final concentration equal to or greater than 1.3M. It is anticipated that other compounds in these and other classes of polyhydroxyl compounds are also effective, and the invention is not to be considered limited to the compounds indicated in the FIGS. presented.

It is also anticipated that mixtures of polyhydroxyl compounds can be prepared, with different proportions of any number of different polyhydroxyl compounds, which would prove to be effective at preventing spontaneous complement activation in a complement-containing sample. For example, a mixture of an effective polyhydroxyl compound, e.g., $\beta$-D-glucose, and one or more ineffective polyhydroxyl compound(s), e.g., inositol and/or D-mannitol, could be mixed with a complement-containing sample to provide protection against spontaneous complement activation during in vitro storage if the final concentration of the effective polyhydroxyl compound was sufficiently high enough to provide protection when present by itself. Therefore, in the case of $\beta$-D-glucose, a final concentration of 1.4–2M in a mixture of polyhydroxyl compounds would be expected to provide full protection against spontaneous complement activation in a complement-containing sample during in vitro storage.

Therefore, in a preferred embodiment, the invention provides a formulation comprising a complement-activation preventive polyhydroxyl compound, as listed above, that when added to the complement-containing sample will provide an effective final concentration of the activation preventive polyhydroxyl compound as also indicated above, together with a divalent cation chelator and an anticoagulant. A preferred embodiment of the invention will contain the divalent cation chelator EDTA at a concentration that when added to a complement-containing sample will provide a final EDTA concentration of between to 40 mM. A preferred embodiment of the invention will contain the anticoagulant sodium heparin at a concentration that when added to a complement-containing sample will provide a final sodium heparin concentration of between 7.5 to 15 IU sodium heparin/mL.

An effective amount of a selected complement-activation preventing substance may be added to a complement-containing sample in a number of ways. The substance, in a formulation together with additives comprising sodium heparin and EDTA, may be provided in appropriate amounts in liquid or crystal form in aliquots for individual samples and packaged in ampoules, packets, vials or similar convenient containers. The substance in these formulations may be included in assay kits for complement proteins. Alternatively, a bulk volume of solution containing the formulation may be incorporated conveniently either as a solution or in the form of dry crystals within an evacuated tube such as, for example, a Vacutainer ™ into which samples of blood are collected. Alternatively, a bulk volume of a solution of the formulation may be provided and an appropriate volume, as a ratio of the sample volume, added to freshly separated plasma or serum or to other freshly collected or freshly prepared sample fluids. As long as the final concentration of each ingredient is within the acceptable range, e.g., EDTA: 1-40 mM; heparin: 15-60 IU/mL; and in the case of β-D-glucose: 1.3M or greater, spontaneous C activation will be prevented in the complement-containing samples as described.

One convenient procedure in which the invention can be employed is to mix the complement-containing sample with an equal volume of an effective invention formulation. Therefore, a particularly preferred embodiment of the invention provides a mixture of 4M β-D-glucose, 40 mM EDTA and 30 IU sodium heparin/mL, pH 7.2+0.2. When a complement-containing sample is mixed with an equal volume of this particularly preferred embodiment of the invention, the final concentration of each of the constituent components will be: β-D-glucose final concentration of 2M, EDTA final concentration of 20 mM, and sodium heparin final concentration of 15 IU/mL. In the remaining portion of the text, this particularly preferred embodiment of the invention will be referred to as Solution B.

Many different experiments were conducted to investigate the effects of incubation time and storage temperature on the spontaneous activation of C in human complement-containing samples stored in vitro with or without the addition of the preferred invention embodiment.

The first set of experiments addressed the question of how long can a human complement-containing sample be incubated at various temperatures in vitro before evidence of spontaneous C activation can be measured. In FIG. 16 results are presented in which freshly drawn EDTA-NHP, heparin plasma, heparin whole blood or EDTA whole blood were stored on ice (1° C.) or at 22° C. After the time periods indicated, samples were collected and stored immediately at −70° C. In the case of the whole blood samples, the cells were removed by centrifugation before the plasma supernatants were collected and stored at −70° C. After all samples had been collected, they were thawed all at once and the C4d fragment levels were quantitated using the C4d fragment EIA. The results indicated that EDTA-NHP samples stored on ice or at 22.C for longer than 2 hr showed clear evidence of spontaneous C4 activation as indicated by the presence of increased levels of C4d fragments. EDTA whole blood showed increased levels of C4d fragments after 2 hr incubation at 22° C. In contrast, plasma or whole blood samples collected in sodium heparin and stored at either 1° C. or 22° C. showed no clear evidence of spontaneous C4 activation over the 6 hour time period studied in this experiment. These results indicated that sodium heparin was able to inhibit spontaneous C4 activation in human complement-containing samples stored at 1° C. or 22° C., at least for as long as 6 hours. These results are in agreement with the data presented in FIG. 13 indicating that addition of sodium heparin to the invention embodiment makes an important contribution to the invention's ability to prevent the spontaneous activation of C4 in a human complement-containing sample. However, as can be seen from the data presented in FIG. 7, heparin alone is not sufficient to prevent the spontaneous activation of C4 in a complement-containing sample incubated in vitro at 22° C for as long as 24 hr. The other components of the invention composition are also required in order to obtain full protection against spontaneous C activation. This point will be covered in further detail below.

The kinetics of spontaneous C3 activation in complement-containing samples was also determined. FIG. 17 presents results in which EDTA-NHP or EDTA whole blood was obtained from 2 different donors (donor A and donor B) and stored on ice, 4° C., 22° C. or in the case of donor B, 37° C. After the time periods indicated, samples were collected and stored immediately at −70° C. In the case of the whole blood sample, the cells were removed by centrifugation before the plasma supernatants were collected and stored at −70° C. After all samples were collected, they were thawed all at once and C3d,g/iC3b fragment levels were quantitated in the donor A samples using the C3d,g/iC3b fragment EIA and iC3b fragment levels were quantitated in the donor B samples using the iC3b fragment EIA. The results indicated that EDTA-NHP obtained from either donor could be stored on ice or at 4.C for at least 6 hr without evidence for the occurrence of spontaneous C3 activation. EDTA-NHP obtained from either donor could be stored at 22° C. for approximately 3 hours without evidence of spontaneous C3 activation. However, samples stored at 22° C. for longer than 3 hr did show indications of spontaneous C3 activation as measured by increased levels of C3d,g/iC3b and iC3b fragment levels. EDTA-NHP from donor B after 2 hr of incubation at 37° C. showed clear evidence of spontaneous C3 activation as measured by increased iC3b fragment levels.

Spontaneous Factor B activation in complement-containing samples was also determined. FIG. 18 presents results in which EDTA-NHP was stored at −20° C., 4° C., 22° C. or 37° C. After the time periods indicated, samples were collected and stored immediately at −70° C. After all samples had been collected, they were thawed all at once and Bb activation fragment levels were quantitated using the Bb fragment EIA. The results indicated that EDTA plasma samples could be stored for as long as 7 days at any of the temperatures studied without evidence of spontaneous Factor B activation.

Spontaneous C activation in normal human serum and EDTA whole blood was also investigated with or without premixing with the preferred invention formulation, (Solution B), i.e., 4M β-D-glucose, 40 mM EDTA, 30 IU sodium heparin/mL. In a typical experiment, normal human serum, EDTA-NHP or EDTA whole blood was mixed with an equal volume of PBS or Solution B and incubated at 22° C. for 48 hr. EDTA-whole blood was also mixed with an equal volume of PBS or Solution B, immediately centrifuged to remove cells and the plasma supernatants (plasma from whole blood) were also incubated at 22° C. for 48 hr. The results from this type of experiment are presented in FIG. 19 and indicate that C4 and C3 spontaneous activation occurred in all samples tested when they were premixed with PBS alone. In general, the amount of C4 and C3 spontaneous activation (as measured by C4d, iC3b and C3d,g/iC3b levels), which occurred in normal human serum premixed with PBS and stored at 22° C. for 48 hr, was significantly greater than measured in EDTA-NHP, EDTA-NHP from whole blood or EDTA whole blood premixed with PBS. This conclusion was confirmed by additional data collected during these studies indicating that spontaneous C activation occurred more rapidly in serum samples as compared to plasma or whole blood samples stored in vitro under the same conditions.

The results presented in FIG. 19, also indicated that premixing each of the four complement-containing samples with Solution B prevented the spontaneous activation of C for 48 hr when stored at 22° C. This conclusion is supported by the percent protection values listed for each of the C fragment assay results for the various complement-containing samples premixed with Solution B. The data obtained for the Bb fragment levels present in the various samples were in agreement with the data presented in FIG. 17 which indicated that Factor B spontaneous activation does not occur in complement-containing serum, plasma or whole blood samples when stored in vitro at 37° C. or below for as long as 7 days.

In addition, Raji Cell CIC Replacement EIA results are also summarized in FIG. 19. The performance of the various complement-containing samples in the Raji CIC EIA should provide an indirect measure of spontaneous C3 activation. As described in the Analytical Methods section, the Raji Cell Replacement CIC EIA test quantitates immune complexes which contain iC3b or C3d,g fragments of C3. When spontaneous C3 activation occurs in a complement-containing sample, iC3b and C3d,g fragments are produced. These iC3b and C3d,g fragments compete for the monoclonal antibody binding sites present on the surface of the microtiter wells used to capture immune complexes containing C3 fragments in the Raji CIC EIA. The competing iC3b and C3d,g fragments produced as the result of spontaneous C3 activation will interfere with immune complex binding and thereby cause an artificial reduction in analyte levels measured. As seen in FIG. 19, when each of the four different samples were premixed with PBS alone, the level of immune complexes detected, as compared with non-incubated time zero control values, were significantly reduced. This can be seen from the percent protection values of greater than 100%. In contrast, when each of the 4 different samples were premixed with Solution B before in vitro storage at 22° C. for 48 hr, no significant change in immune complex levels was observed.

The spontaneous activation of complement was also determined in freshly drawn human plasma samples using different anticoagulants to prevent clot formation. Thus, plasma samples were prepared using EDTA (10 mM final EDTA concentration), sodium citrate (8 mM final sodium citrate concentration), or sodium heparin (5 IU/mL final sodium heparin concentration). Each freshly prepared plasma sample was mixed with an equal volume of PBS (untreated) or the preferred embodiment of the invention, Solution B, and incubated at 22° C. Samples were collected after 0, 24 and 48 hr of incubation and frozen immediately at −70° C. When all samples had been collected, they were thawed all at once and C4d and iC3b fragment levels were quantitated using the C4d and iC3b fragment EIA tests. The C4d fragment results, seen in FIG. 7, indicated that of the three untreated plasma samples tested, EDTA-NHP exhibited by far the highest level of spontaneous C4 activation. Heparin-NHP exhibited an intermediate level of spontaneous C4 activation, while citrated-NHP showed the lowest level of spontaneous C4 activation. Nevertheless, after 24 hr in vitro storage at 22° C., all three untreated plasma samples exhibited significantly elevated levels of C4d fragments as compared with the corresponding non-incubated time zero control. However, if the plasma samples were premixed with an equal volume of Solution B before in vitro storage at 22° C., no spontaneous C4 activation occurred over the 48 hr time period studied as measured by the appearance of C4d fragments.

Figure 8:
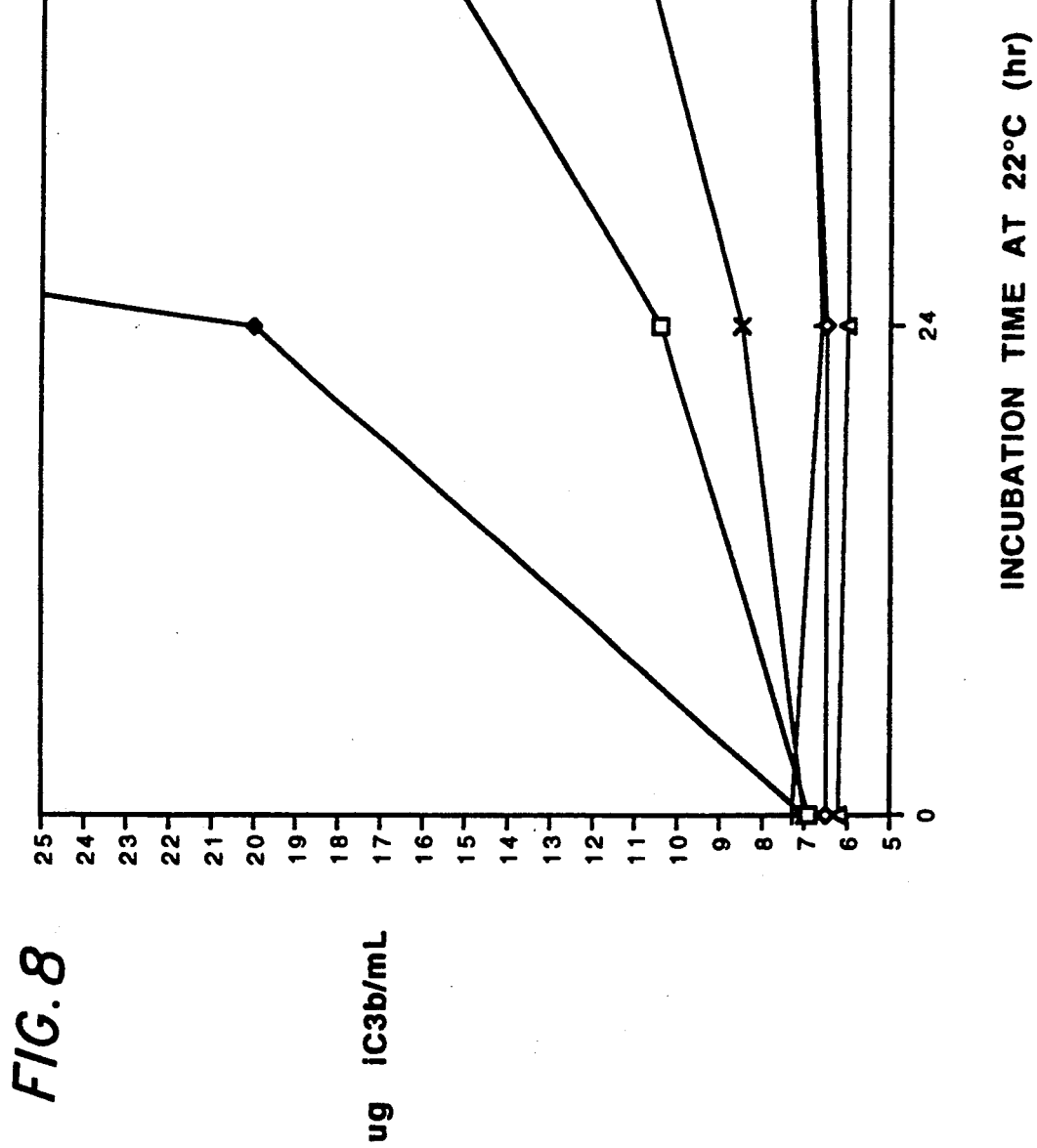
FIG. 8. Prevention of spontaneous C3 activation in normal human plasma collected in EDTA, citrate or heparin anticoagulant. Normal human plasma was prepared from blood collected into vacutainer TM tubes containing sodium EDTA, sodium citrate or sodium heparin as the anticoagulant. Each freshly prepared plasma sample was mixed together with an equal volume of either PBS or Solution B and stored at 22° C. After the time periods indicated, samples were collected and stored at −70° C. The collected samples were thawed all at once and spontaneous C3 activation was quantitated using the iC3b fragment EIA. The results are shown as µg iC3b/mL present in each experimental plasma sample as a function of time. Plasma incubation conditions: EDTA-NHP mixed with PBS (open square symbols); EDTA-NHP mixed with Solution B (plus (+) symbols); sodium citrate plasma mixed with PBS (X symbols); sodium citrate plasma mixed with Solution B (inverted open triangle symbols); sodium heparin plasma mixed with PBS (open diamond symbols); sodium heparin plasma mixed with Solution B (open triangle symbols).

The iC3b fragment results, seen in FIG. 8, indicated that of the three untreated plasma samples tested, the heparin-NHP sample exhibited by far the highest level of spontaneous C3 activation. EDTA-NHP exhibited an intermediate level of spontaneous C3 activation while citrated-NHP showed the lowest level of spontaneous C3 activation. However, after 24 hr incubation at 22° C., all three untreated plasma samples exhibited significantly elevated levels of iC3b fragments as compared with the corresponding non-incubated time zero control. In analogy with the C4d fragment results observed in FIG. 7, when each of the three different plasma samples were premixed with an equal volume of Solution B before in vitro storage at 22° C., no spontaneous C3 activation occurred over the 48 hr time period studied as measured by the iC3b fragment EIA results. In addition, similar results were obtained for these plasma samples when the C3d,g/iC3b fragment levels were determined using the C3d,g/iC3b fragment EIA (data not shown).

The effect of pre-dilution of a complement-containing sample on spontaneous C activation was also determined. The results from a representative experiment are presented in FIG. 20 in which a freshly drawn EDTA-NHP plasma sample was pre-diluted on ice with ice cold PBS containing 10 mM EDTA (PBSE) by the following dilution factors: 0, 1:1, 1:2, 1:3, 1:4 and 1:5. All pre-diluted EDTA-NHP samples were mixed thoroughly and subsequently added to an equal volume of PBS (untreated) or Solution B (treated).

After mixing again, all samples were stored at 22° C. After the time periods indicated, samples were collected and transferred immediately to −70° C. storage. When all samples were collected, they were thawed all at once and assayed for C4d and C3d,g/iC3b levels using the C4d and C3d,g/iC3b EIA kits. However, since several different pre-dilution factors were used in this experiment, different dilutions of the collected samples were used in the EIA kits in order to quantitate the C4d and C3d,g/iC3b levels in each sample. For example, a 1:100 final dilution of a plasma specimen is recommended to be used in the C4d fragment EIA. Therefore, an EDTA-NHP sample that was not pre-diluted with PBSE (a pre-dilution factor of 0) but was diluted with an equal volume of PBS (untreated) before storage at 22° C., was diluted 1:50 in C4d specimen diluent to provide a final 1:100 dilution of this sample to be assayed in the C4d EIA. On the other hand, an EDTA-NHP sample that was prediluted 1:5 in PBSE, then diluted in an equal volume of Solution B (treated) before storage at 22.C, was diluted 1:10 in C4d specimen diluent to also provide a final 1:100 dilution of this sample to be assayed in the C4d EIA kit. EDTA-NHP samples that were tested in the C3d,g/iC3b fragment EIA were diluted in C3d,g/iC3b specimen diluent by the dilution factor necessary to provide a final EDTA-NHP dilution of 1:250 to be assayed in the C3d,g/iC3b fragment EIA.

The results presented in FIG. 20 indicated that EDTA-NHP samples could be premixed in PBSE over the dilution range studied, subsequently mixed with an equal volume of PBS (untreated) or Solution B (treated) and frozen immediately (time zero controls) without influencing the C4d fragment levels measured/mL. However, this was not the case for C3d,g/iC3b fragment levels present in EDTA-NHP samples treated in a similar manner. For example, an EDTA-NHP sample that was not pre-diluted with PBSE, mixed with an equal volume of PBS and frozen immediately at $-70°$ C., contained 2.7 $\mu$g C3d,g Eq/mL. In contrast, a portion of the original EDTA-NHP sample that was pre-diluted 1:5 with PBSE, mixed with an equal volume of PBS and frozen immediately at $-70°$ C., contained 12.0 $\mu$g C3d,g Eq/mL. As seen in FIG. 20, as the pre-dilution factor increased, the amount of spontaneous C3 activation observed in these EDTA-NHP samples also increased. The mechanism by which this spontaneous C3 activation occurred in the EDTA-NHP samples which were prediluted in physiological buffered saline solutions followed by freezing and thawing at $-70°$ C., is unknown. However, the data presented in FIG. 20 indicated clearly that subsequent addition of an equal volume of Solution B to these pre-diluted complement-containing samples was not able to prevent the spontaneous C3 activation observed. However, if Solution B was added to the EDTA-NHP sample that was not pre-diluted with PBSE, spontaneous C3 activation was prevented completely even if the specimen was stored at 22° C. for as long as 48 hr (refer to the $\mu$g C3d,g Eq/mL values determined for the treated EDTA-NHP samples listed in FIG. 20).

In conclusion, EDTA-NHP samples that are prediluted as much as 1:5 with physiological buffered saline can be mixed with an equal volume of Solution B and stored at 22° C. for at least 48 hr without any evidence of spontaneous C4 activation. The same is true for Factor B in these samples (data not shown). However, in order to prevent the spontaneous activation of C3, complement-containing samples cannot be pre-diluted before mixing with Solution B. The iC3b EIA results were similar to the C3d,g fragment results seen in FIG. 20 (data not shown).

In using the preferred embodiment of this invention, the only known special requirement for its use to prevent spontaneous C activation in a complement-containing sample is detailed above in the results presented in FIG. 20. Namely, in order to inhibit the spontaneous activation of C3, Solution B must be mixed with a complement-containing sample which has not been pre-diluted.

We have found that a complement-containing sample can be mixed with an equal volume of Solution B and stored in a container of any size, shape or material composition. The majority of the test results presented in this study were obtained by using containers made of borosilica glass, polypropylene, polycarbonate or polystyrene. Removal of air or replacement of air with nitrogen or any other gas in the storage container is not necessary.

There are however, certain limitations to the ability of a particularly preferred embodiment of the invention to prevent the spontaneous activation of C in a complement-containing sample. In general, the longer the time period a complement-containing sample is stored in vitro, the greater the incident of spontaneous C activation that will occur. Also, the higher the in vitro storage temperature at which a complement-containing sample is stored, the greater the incident of spontaneous C activation. These same general concepts also are true regarding storage of a complement-containing sample mixed together with a preferred embodiment of the invention. Namely, the longer the storage time and the higher the storage temperature, the greater the incident of spontaneous C activation, even in a complement-containing sample containing optimal final concentrations of the preferred embodiment of the invention. However, when a complement-containing sample is mixed with a preferred embodiment of the invention, the rate of spontaneous C activation will be greatly decreased. In fact, the ability of a preferred embodiment of the invention to decrease the rate of spontaneous C activation in a complement-containing sample allows for the in vitro storage of complement-containing samples at conventional storage temperatures for periods as long as several weeks preliminary to assay, without causing erroneous C assay results.

Data obtained in these studies concerning the occurrence of spontaneous C activation in untreated complement-containing samples upon in vitro storage at $-20°$ C. to 37° C. are summarized in FIG. 21. A definite trend can be identified from the data presented in FIG. 21. Namely, the higher the temperature of storage, the greater the rate of spontaneous C activation detectable. However, there is one exception. That is, complement-containing samples stored at $-20°$ C. always showed high levels of spontaneous C3 activation, as measured by increased concentrations of iC3b and C3d,g/iC3b fragments, even if the storage time is relatively short, e.g., one freeze/thaw cycle after 1 hour of sample storage at $-20°$ C.

Data regarding the ability of the preferred embodiment of the invention to prevent spontaneous complement activation in a complement-containing sample is summarized in FIG. 22. The majority of the data presented in FIG. 22 was summarized from the data presented in this application. By comparing the data presented in FIG. 22 with the results presented in FIG. 21, it is apparent that when an effective amount of a preferred embodiment of the invention is added to complement-containing samples, these samples can be stored in vitro at conventional temperatures, i.e., stored frozen at $-1°$ C. to $-20°$ C. or stored in liquid form refrigerated at $+1°$ C. to $+14°$ C. or in liquid form at room temperature, for several days preliminary to assay, without introducing erroneous results. For example, an untreated EDTA-NHP sample can be stored at 22° C. for no longer than 3 hr before evidence of spontaneous C3 activation can be detected. In contrast, EDTA-NHP samples which were mixed with an effective amount of a preferred embodiment of the invention can be stored at 22° C. for a minimum of 7 days without evidence of spontaneous C3 activation.

Since the preferred embodiment of the invention is able to prevent the spontaneous activation of complement in a complement containing sample when stored in vitro over a wide range of temperature conditions, this method can therefore be used to improve the quality of the results and thereby improve the performance of any assay procedure used to measure the concentration of a functionally active C protein or a complement protein physiological activation fragment present in a complement-containing sample. Thus, use of the invention will improve the performance of a wide variety of C assay procedures, e.g., the commercially available monoclonal antibody based EIA tests from Cytotech, Inc. (San Diego, Calif.) which quantitate the levels of a variety of complement protein activation fragments and complexes, the commercially available RIA kits from Amersham International, Amersham U.K., which quantitate the levels of the C4a, C3a and C5a anaphylatoxin activation peptides of human C activation, and the commercially available monoclonal antibody EIA kits to quantitate the levels of CIC containing C3 fragments from Cytotech, Inc., San Diego, Calif., and Immunomedics, Newark, N.J. In addition to these commercially available complement assays, the use of this invention would also improve the performance of a wide variety of common research, and perhaps clinical, lab procedures, e.g., one dimensional immunoelectrophoresis, two dimensional (crossed) immunoelectrophoresis, intermediate gel two-dimensional immunoelectrophoresis, rocket immunoelectrophoresis, countercurrent immunoelectrophoresis and a variety of immunotransfer and blotting procedures.

The coagulation system of blood plasma proteins has many properties in common with the complement system. Both systems represent a cascading, amplification system of proteins in which precursor proteins, usually protein zymogens, are converted from inactive circulating forms to active forms. In analogy with the complement system, the coagulation system of blood plasma proteins can be triggered and activated by a variety of biological ssubstances via two pathways of activation, the intrinsic pathway and the extrinsic pathway. Physiological activation of both the complement and the coagulation systems require assembly of protein complexes on surfaces in an ordered and defined sequence of reaction steps. Activation of the complement system occurs on a variety of target surfaces as described above, while activation of the coagulation system occurs on the outer membrane surface of blood platelets. In addition, key reaction steps which occur in both the coagulation and the complement systems are modulated by a variety of naturally occurring plasma regulatory proteins. As the result of these control mechanisms, activation of either the complement or the coagulation system of proteins results in the generation of physiological protein fragments which accumulate in the fluid-phase as inactive catabolic byproducts of activation.

Similar to the complement system, spontaneous activation of the coagulation system in plasma samples upon in vitro storage represents a major problem for the measurement of coagulation component or pathway functional activity. Thus, for measuring the Activated Partial Thromboplastin Time (APTT) and the Partial Thromboplastin Time (PTT), it is recommended that plasma be prepared from citrated whole blood immediately after collection and the APTT or PTT determinations must be conducted within one hour if reliable results are to be obtained. If the APTT or PTT determinations can not be done within one hour, the plasma samples must be stored frozen, In: *Clinical Guide to Laboratory Tests*. N. W. Tietz, (ed). W. B. Saunders Company, Philadelphia. 1983. pp. 10 and 372.

In addition to these numerous similarities, the complement and coagulation systems actually share common protein factors in certain reaction steps. For example: 1) activated Hageman Factor (FXIIa) of the coagulation system can activate the Cl complex of the complement system, M. Silverberg and A. P. Kaplan. Adv. Inflammation 2:165-185 (1981), 2) Cl-Inhibitor, besides being the major plasma inhibitor of activated Clr and Cls of the complement system, is also an effective inhibitor of plasma kallikrein, Factor XIIa, as well as the physiological, enzymatically active catabolic fragments derived from Factor XIIa known as Factor XIIf, A. E. Davis. Ann. Rev. Immunol. 6:595-628 (1988), 3) activated complement Factor B is able to cleave and activate prothrombin and plasminogen, J. S. Sundsmo and D. S. Fair. Springer Semin. Immunopath. 7:379-406 (1984), 4) the terminal components of complement, C5 through C9, are activated on the surface of platelets by a thrombin dependent mechanism during clot formation in human blood, M. J. Polley and R. L. Nachman, J. Exp. Med. 150:633-645 (1979), and 5) thrombin, kallikrein and plasmin have been reported to cleave and activate several complement component proteins including C4, C3 and C5, J. S. Sundsmo and D. S. Fair. Springer Semin. Immunopath. 7:379-406 (1984). Since the complement and coagulation systems of blood plasma share a large number of biochemical and regulatory features, including the occurrence of spontaneous activation reactions during storage in vitro, it may be presumed that the ability of the described invention to prevent the spontaneous activation of the complement system would also prevent the spontaneous activation of the coagulation system upon storage in vitro.

ANALYTICAL METHODS

During the course of these studies, RIA or EIA procedures were conducted to quantitate the following complement physiological activation products: C3a anaphylatoxin, C4d, iC3b, C3d,g/iC3b, Bb and SC5b-9 complex. In addition, levels of circulating immune complexes were also quantitated using a Raji Cell Replacement EIA.

C3a anaphylatoxin levels were quantitated by using a commercially available RIA kit purchased from Amersham International, Amersham, UK. The C3a RIA is based on a competitive reaction between $^{125}$I-C3a des Arg and unlabeled C3a and C3a des Arg (input from the test specimen) for a limited number of specific rabbit antibody binding sites. C3a des Arg is the designation used to identify the naturally occurring derivitive of C3a found in circulating blood plasma in which the carboxyl-terminal arginine amino acid residue number 77 has been enzymatically cleaved and removed from the C3a peptide by serum carboxypeptidase N. T. E. Hugli, Contemp. Topics Molec. Immunol. 7:181-214 (1978). The antibody-bound C3a fraction is reacted with goat anti-rabbit IgG, the immune precipitate is separated by centrifugation, and the radioactivity present in the pellet is determined. Since the input of specific rabbit antibody and $^{125}$I-C3a des Arg is fixed, the amount of $^{125}$I-C3a des Arg bound to the pelleted antibody fraction will be inversely proportional to the concentration of added unlabeled competing ligand. The concentration of unlabeled C3a and C3a des Arg present in a given test specimen is determined by interpolation from a standard curve. Similar C3a RIA assay procedures have been published and have been in use for several years, J. L. Wagner and T. E. Hugli, Analyt. Biochem. 136:75-88 (1984).

All of the EIA tests employed in these studies utilized solid-phase monoclonal antibody capture assay kit procedures (Cytotech, Inc., San Diego, Calif.). The procedure was basically the same for each EIA kit. Briefly, in the first step of each EIA assay, 100 μL of standards, controls and diluted test specimens were incubated at 22° C., i.e., room temperature, in duplicate polystyrene microtiter wells precoated with a capture monoclonal antibody which specifically reacted with the complement fragment or complex under investigation. During this first incubation period, complement fragments or complexes were bound to the monoclonal antibody coated microassay wells. A wash cycle removed unbound materials.

In the second step, 50 μL of horseradish peroxidase (HRP)-conjugated purified IgG antibody, which reacted with the captured complement fragment or complex analyte, was added to each well and incubated at 22° C. A wash cycle removed unbound conjugate.

In the third step, 100 μL of the HRP enzyme substrate ABTS (0.034% ABTS and 0.0126% $H_2O_2$ in 100 mM sodium citrate buffer, pH 4.0) was added to each well and incubated at 22° C. The bound HRP-conjugated antibody reacted with the ABTS substrate producing a green color which was proportional to the amount of specimen analyte bound. The HRP-enzymatic reaction was stopped upon addition of 50 μL 250 mM oxalic acid. The substrate color intensity present in each well was measured at 405 nm using an automated EIA microplate reader and the analyte concentration/mL in the original test specimen was determined for each analyte from the appropriate standard curve.

The following is detailed information unique to each EIA kit procedure:

C4d EIA: The capture mouse monoclonal antibody used to coat microtiter wells for the C4d fragment EIA was Cytotech MoAb 057-51.5.1.5.9 which reacts with a neoantigenic determinant expressed by C4d and C4b activation fragments of human C4. MoAb 057-51.5.1.5.9 does not react with native C4 in free solution or with the C4c fragment. The C4d fragment EIA was performed using the following incubation times: specimen incubation time was 30±1 min; HRP-conjugate (mouse MoAb anti-human C4d) incubation time was 30±1 min; ABTS substrate incubation time was 30±1 min. A 1:100 dilution of all plasma or serum samples was used in the C4d fragment EIA tests.

iC3b EIA: The capture mouse monoclonal antibody used to coat microtiter wells for the iC3b fragment EIA was Cytotech MoAb 013III-1.1.6.1 which reacts with a neoantigenic determinant expressed on the iC3b activation fragment of human C3. MoAb 013III-1.1.6.1 does not react with native C3 in free solution or with the C3b, C3c, C3d,g, C3e, C3f or C3g fragments of human C3. The iC3b fragment EIA was performed using the following incubation times: specimen incubation time was 30±1 min; HRP-conjugate (goat anti-human C3 IgG) incubation time was 30±1 min; ABTS substrate incubation time was 30±1 min. A plasma dilution of 1:50 and a serum dilution of 1:100 were used in the iC3b fragment EIA tests. The immunochemical reaction specificity of MoAb 013III-1.1.6.1 has been published previously in abstract form, W. P. Kolb, et al., Fed. Proc. 44:990 (1985).

C3d,o/iC3b EIA: The capture mouse monoclonal antibody used to coat microtiter wells for the C3d,g/iC3b fragment EIA was Cytotech MoAb 013III-31.4.3.2.2 which reacts with a neoantigenic determinant expressed on the iC3b, C3d,g and C3d activation fragments of human C3. MoAb 013III-31.4.3.2.2 does not react with native C3 in free solution or with the C3c, C3e, C3f or C3g fragments of C3. The C3d,g/iC3b fragment EIA was performed using the following incubation times: specimen incubation time was 60±1 min; HRP-conjugate (rabbit anti-human C3d IgG) incubation time was 30±1 min; ABTS substrate incubation time was 30±1 min. A plasma dilution of 1:250 and a serum dilution of 1:500 were used in the C3d,g/iC3b EIA tests. Production of a monoclonal antibody specifically reactive with a neoantigenic determinant on iC3b, C3d,g and C3d activation fragments of human C3 has been reported previously in the published complement literature, J. D. Tamerius, et al., J. Immunol. 135:2015–2019 (1985); Y. Kanayama, et al., J. Immunol. Meth. 88:33–36 (1986). The immunochemical reaction specificity of the Cytotech MoAb 013III-31.4.3.2.2 has been published previously in abstract form, W. P. Kolb, et al., FASEB Journal 2:A1834 (1988).

Bb EIA: The capture mouse monoclonal antibody used to coat microtiter wells for the Bb fragment EIA was Cytotech MoAb 032B-22.1.2.1 which reacts with a neoantigenic determinant expressed on the Bb activation fragment of human Factor B. MoAb 032B-22.1.2.1 does not react with native Factor B in free solution or with the Ba activation fragment. The Bb fragment EIA was performed using the following incubation times: specimen incubation time was 30±1 min; HRP-conjugate (goat anti-human Factor B) incubation time was 30±1 min; ABTS substrate incubation time was 30±1 min. A plasma dilution of 1:25 and a serum dilution of 1:50 were used in the Bb fragment EIA tests. The use of a monoclonal antibody specifically reactive with a neoantigenic determinant to quantitate the Bb activation fragment of Factor B is proprietary technology to Cytotech, Inc. That is, the existence of a Bb fragment neoantigenic determinant, as defined by monoclonal antibody reactivity, has not been reported to date in the complement research literature except by Cytotech researchers. The immunochemical reaction specificity of MoAb 032B-22.1.2.1 has been reported previously in abstract form, W. P. Kolb, et al., Complement 4:181 (1987).

SC5b-9: The capture mouse monoclonal antibody used to coat microtiter wells for the quantitative SC5b-9 complex EIA was Cytotech MoAb 056B-75.2.3.1.3 which reacts with a neoantigenic determinant present within the poly-C9 portion of the assembled SC5b-9 complex. MoAb 056B-75.2.3.1.3 does not react with native C9 in free solution or with any of the other SC5b-9 complex precursor proteins. The SC5b-9 complex EIA was performed using the following incubation times: specimen incubation time was 60±1 min; HRP-conjugate (a mixture of goat anti-human C6 and C7 IgG) incubation time was 60±1 min; ABTS incubation time was 30±1 min. Production of monoclonal antibodies specifically reactive with a neoantigenic determinant on the SC5b-9 complex has been reported previously in the published complement literature, T. E. Mollnes, et al., Scand. J. Immunol. 22:197–202 (1985); R. J. Falk, et al., J. Clin. Invest. 72:560–573 (1983); R. J. Falk, et al., N. Engl. J. Med. 312:1594–1599 (1985); F. Hugo, et al., J. Immunol. Meth. 99:243–251 (1987).

Raji Cell Replacement EIA: The Raji Cell Replacement (RCR) EIA is an EIA procedure for the quantitation of circulating immune complexes which have iC3b or C3d,g activation fragments of C3 covalently bound to them. The capture mouse monoclonal antibody used to coat microtiter wells for the quantitation of circulating immune complexes containing C3 activation fragments was Cytotech MoAb 053A-514.3.1.4 which reacts with a neoantigenic determinant present on iC3b, C3d,g and C3d activation fragments of human C3. MoAb 053A-514.3.1.4 does not react with native C3 in free solution or the C3c, C3e, C3f or C3g fragments of C3. Therefore, MoAb 053A-514.3.1.4 has the same C3 fragment reaction specificity as the CR2 complement receptor present on the Raji B-lymphocyte cell line, G. D. Ross and M. E. Medof, Adv. Immunol. 37:217–267 (1985), and the same C3 fragment reaction specificity as MoAb 013III-31.4.3.2.2 described above for the Cytotech, Inc. C3d,g/iC3b fragment EIA. The RCR CIC EIA was performed using the following incubation times: specimen incubation time was 60±1 min; HRP-conjugate (mouse anti-human IgG) incubation time was 30 ±1 min; ABTS incubation time was 30±1 min.

EXAMPLES

Figure 9A:
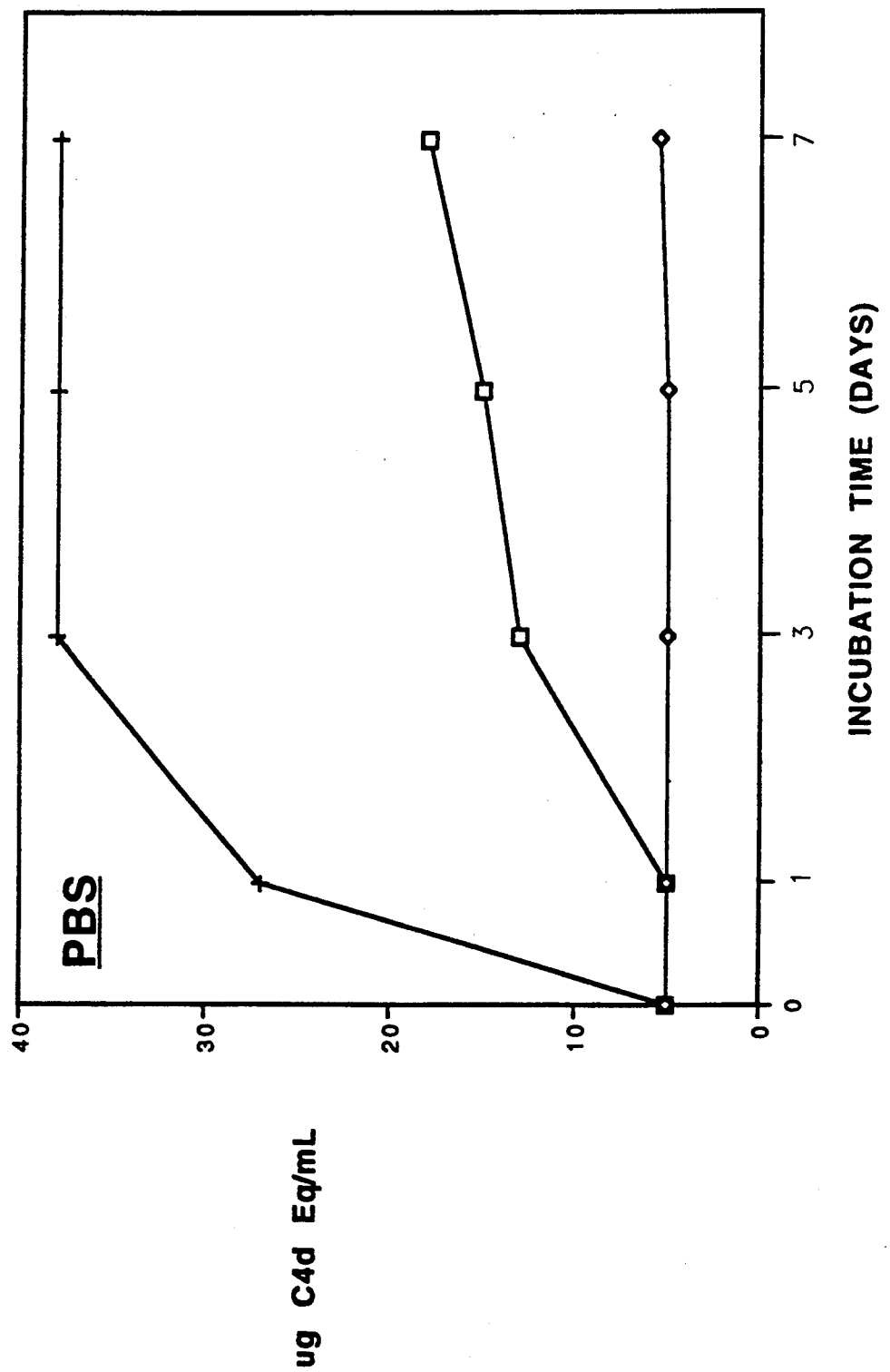
FIGS. 9A and 9B: Prevention of spontaneous C4 activation in EDTA normal human plasma. EDTA-NHP was mixed with an equal volume of either PBS (FIG. 9A) or Solution B (FIG. 9B) and stored at −20° C., 4° C., or 22° C. After the time periods indicated, samples were collected and stored at −70° C. Collected samples were thawed all at once and spontaneous C4 activation was quantitated using the C4d fragment EIA. The results are shown as µg C4d equivalents/mL present in each experimental plasma sample as a function of time. Incubation conditions: −20° C. (open diamond symbols); 4° C. (open square symbols); 22° C. (plus(+) symbols).
Figure 9B:
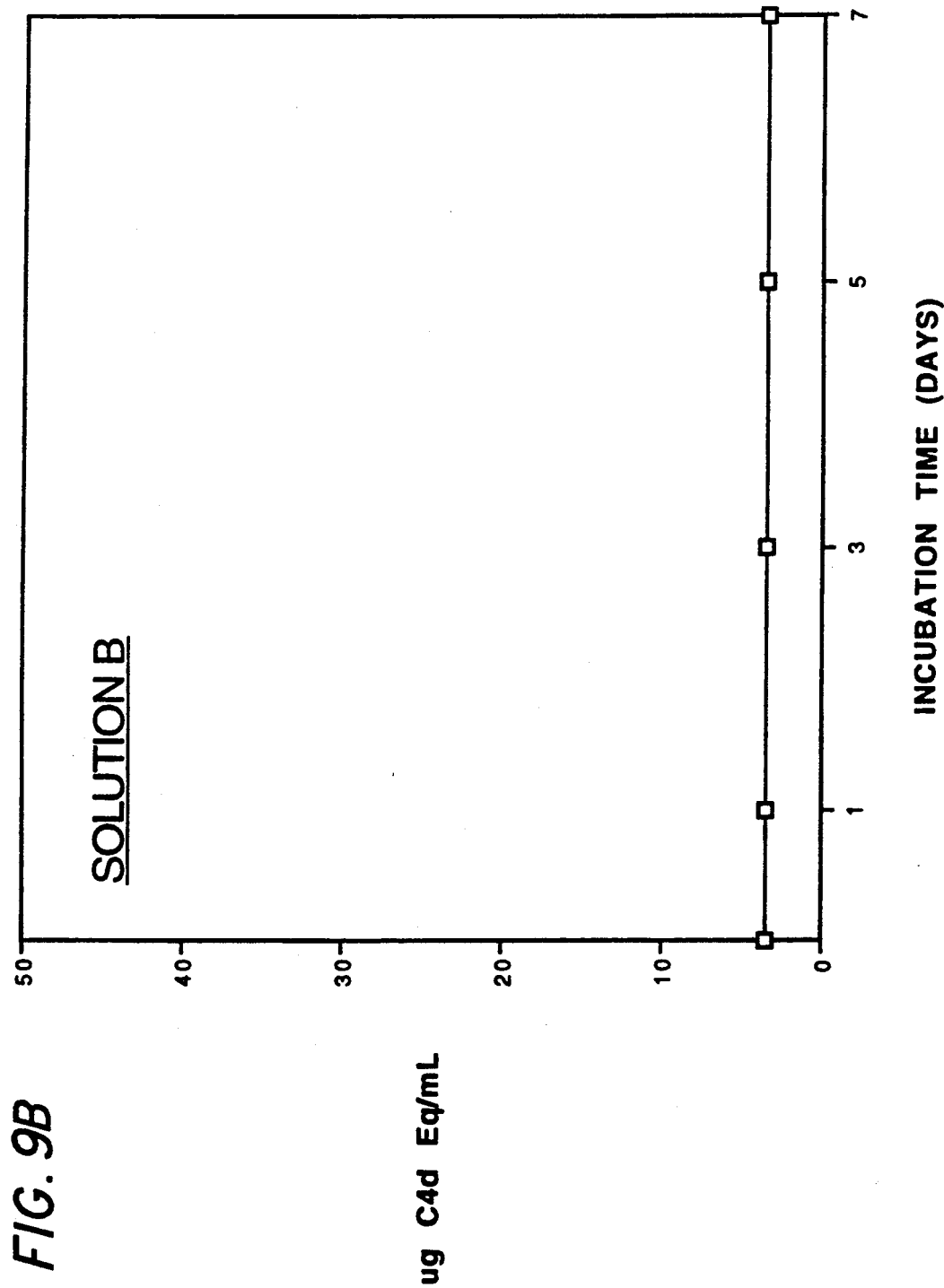

A preferred embodiment of the invention, i.e., 4M β-D-glucose, 40 mM EDTA and 30 IU/mL sodium heparin dissolved in deionized water (Solution B) was mixed with an equal volume of freshly drawn EDTA-NHP and stored at −20° C., 4° C., 22° C. or 37° C. Portions of the same freshly drawn EDTA-NHP sample was mixed with an equal volume of PBS (untreated) and also stored at −20° C., 4° C., 22° C. or 37° C. Samples were obtained on days 0, 1, 3, 5 and 7 and frozen immediately at −70° C. After all samples had been collected, they were thawed all at once and the C4d and iC3b fragment levels were quantitated using the C4d and iC3b fragment EIA kits. The data in FIG. 9 presents the C4d fragment assay results which indicated that untreated EDTA-NHP samples could be stored at −20° C. for 7 days or at 4° C. for 1 day before evidence of spontaneous C4 activation could be measured. The results presented in FIG. 9 are in agreement with the data presented in FIG. 16 indicating that untreated EDTA-NHP samples can not be stored at 22° C. for more than 2 hr without the occurrence of spontaneous C4 activation. In contrast, as seen in FIG. 9, EDTA-NHP samples treated with Solution B could be stored at −20° C., 4° C. or 22° C. for a minimum of 7 days without showing evidence of spontaneous C4 activation.

Figure 10A:
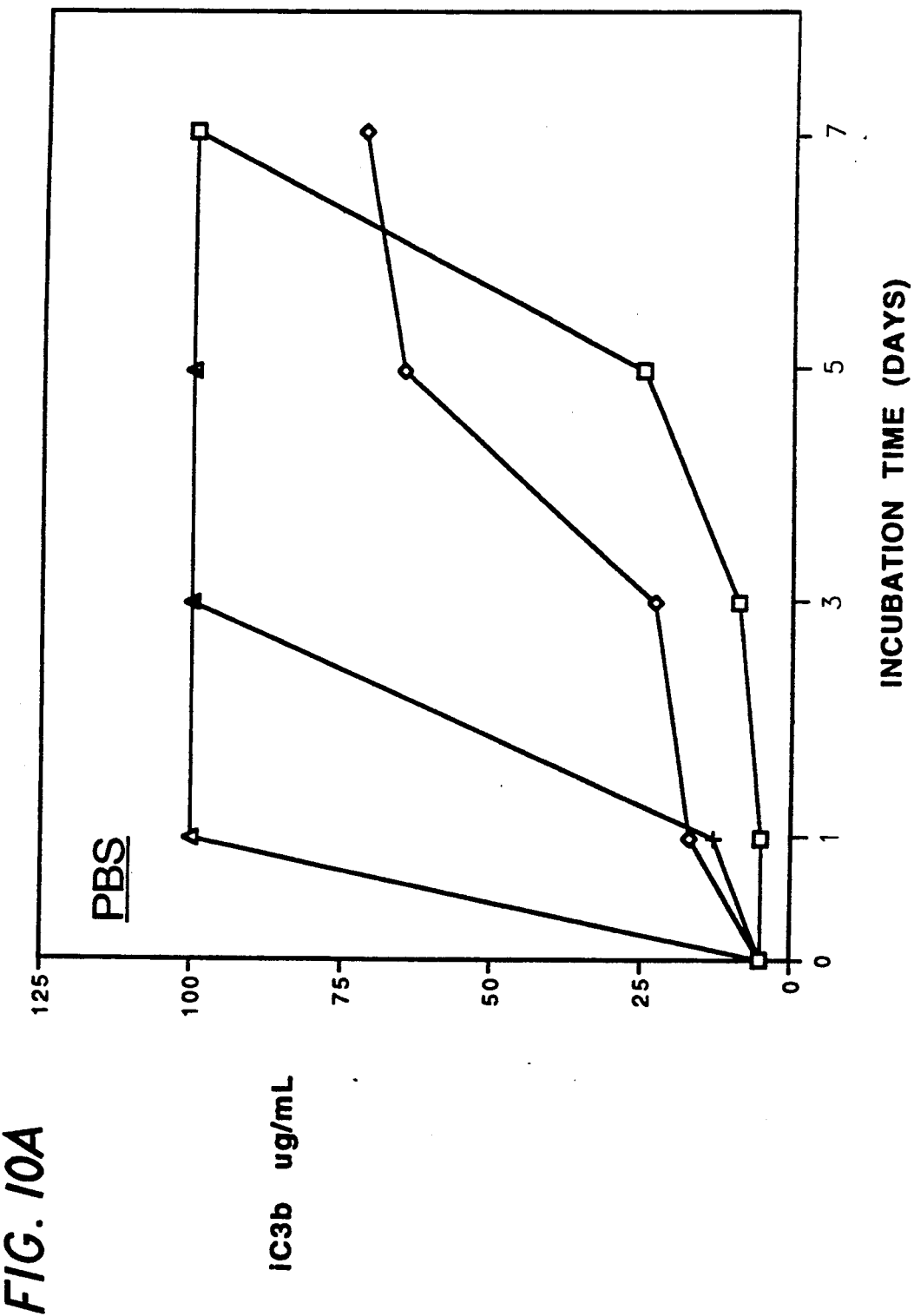
FIGS. 10A and 10B: Prevention of spontaneous C3 activation in EDTA normal human plasma. EDTA-NHP was mixed with an equal volume of PBS (FIG. 10A) or Solution B (FIG. 10B) and stored at −20° C., 4° C. or 37° C. After the time periods indicated, samples were collected and stored at −70° C. the collected samples were thawed all at once and spontaneous C3 activation was quantitated using the iC3b EIA. the results are show as µg iC3b/mL present in each experimental plasma sample. Incubation condition: −20° C. (open diamond symbols); 4° C. (open square symbols); 22° C. (plus (+) symbols); 37° C. (open triangle symbols).
Figure 10B:
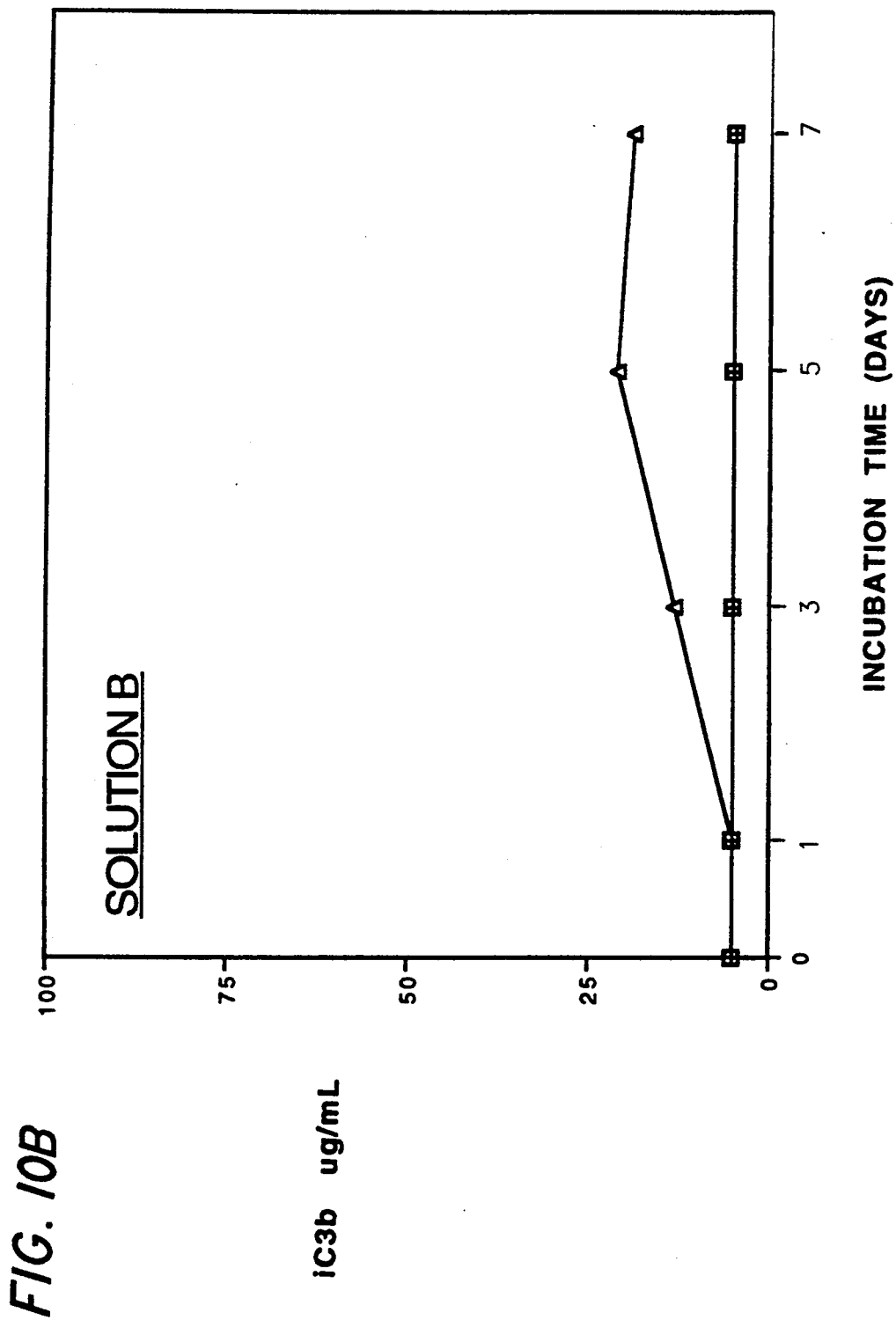

The data in FIG. 10 presents the iC3b fragment assay results which indicated that untreated EDTA-NHP samples could be stored at 4.C for 1 day without showing evidence of spontaneous C3 activation. The results presented in FIG. 10 are in agreement with the data presented in FIG. 17, indicating that untreated EDTA-NHP samples could not be stored at 22° C. for more than 4 hr or at 37° C. for more than 1 hr without the occurrence of spontaneous C3 activation. In contrast, EDTA-NHP samples treated with Solution B could be stored at −20° C., 4° C. or 22° C. for a minimum of 7 days without showing any evidence of spontaneous C3 activation as measured in the iC3b fragment EIA. EDTA-NHP samples premixed with Solution B could be stored at 37° C. for as long as 24 hr without showing increased iC3b fragment levels. Results similar to those shown in FIG. 10 using the iC3b EIA were also obtained when these same EDTA-NHP samples were assayed for C3a and C3d,g/iC3b levels using the C3a RIA or the C3d,g/iC3b EIA kits.

A similarly designed experiment was conducted in which spontaneous C activation was studied employing the Raji Cell Replacement (RCR) CIC EIA test. The rationale for using the RCR CIC EIA in these C activation studies is discussed in detail in the text describing the data presented in FIG. 19. The experimental data seen in FIG. 11 was obtained with a RCR CIC EIA positive EDTA-human plasma sample, obtained from an SLE patient, which was mixed with an equal volume of PBS (untreated) or Solution B. Portions of these mixtures were stored at −20° C., 4° C. or 22° C. and after the time periods indicated, samples were collected and stored at −70° C. The collected samples were thawed all at once and the level of immune complexes containing C3 physiological breakdown fragments (iC3b/C3d,g:IgG complexes) in each experimental sample was quantitated using the RCR CIC EIA. The results seen in FIG. 11 indicated that when an untreated EDTA plasma sample with elevated levels of CIC, was stored frozen at −20° C., an increase in the levels of iC3b/C3d,g:IgG complexes was seen. This apparent increase in CIC was similar to the increase in iC3b levels seen in untreated EDTA-NHP samples which had been stored at −20° C. (refer to results presented in FIG. 10). The most likely explanation for these observations is that freezing and thawing of EDTA-NHP samples at −20° C. resulted in the hydrolysis of the C3 internal thiol ester bond, with the resultant formation of $C3(H_2O)$. A certain percentage of the nascent $C3(H_2O)$ molecules would be able to bind to adjacent protein molecules in solution, e.g., IgG, to form $C3(H_2O)$:IgG complexes. The $C3(H_2O)$ bound to the IgG molecules would be fragmented to $iC3(H_2O)$ and bound by the capture MoAb coating the RCR CIC EIA plates. This hypothesis would explain the increase in analyte signal in the sample stored at −20° C. as detected in the RCR CIC EIA. This hypothesis is supported by the observation that C3 fragment:IgG complexes are generated in normal human serum during C3 activation by a wide variety of C activators including aggregated human IgG, zymosan and cobra venom factor, A. van Dam and C. E. Hack, Complement 3:219 (1986).

Figure 11A:
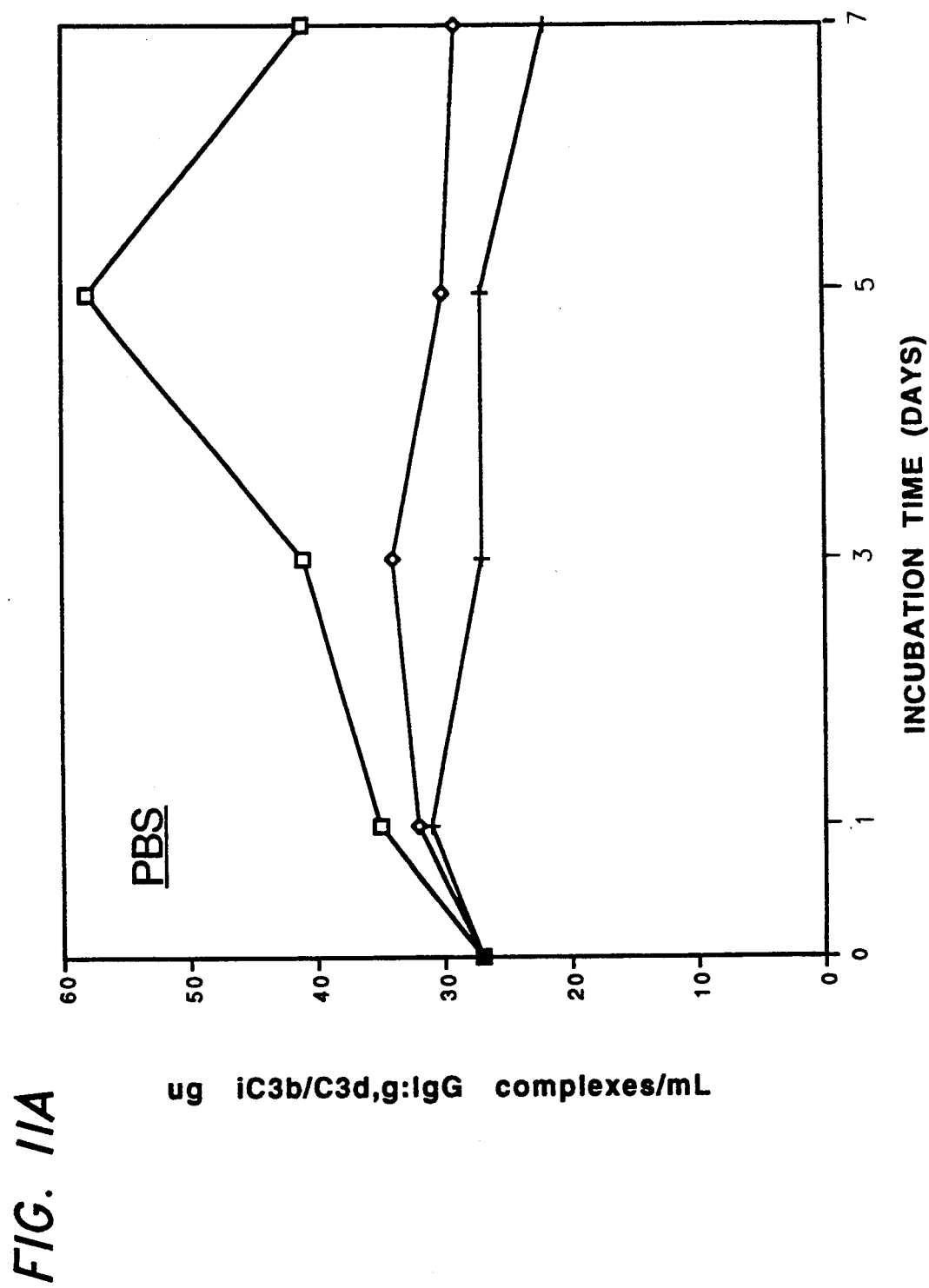
FIGS. 11A and 11B. Prevention of spontaneous complement activation in an EDTA human plasma specimen containing abnormally elevated levels of circulating immune complexes. An EDTA human plasma sample containing elevated levels of CIC was mixed with an equal volume of PBS (FIG. 11A) or Solution B (FIG. 11B) and stored at −20° C., 4° C. or 22° C. After the time periods indicated, samples were collected and stored at −70° C., The collected samples were thawed all at once and the formation of C3 fragment: Ig complexes was quantitated using the Raji Cell Replacement EIA. The results are presented at µg iC3b/C3d, g:IgG complexes mL present in each experimental plasma sample as a function of time. Incubation conditions: −20° C. (open square symbols); 4° C. (open diamond symbols) 22° C. (plus (+) symbols).
Figure 11B:
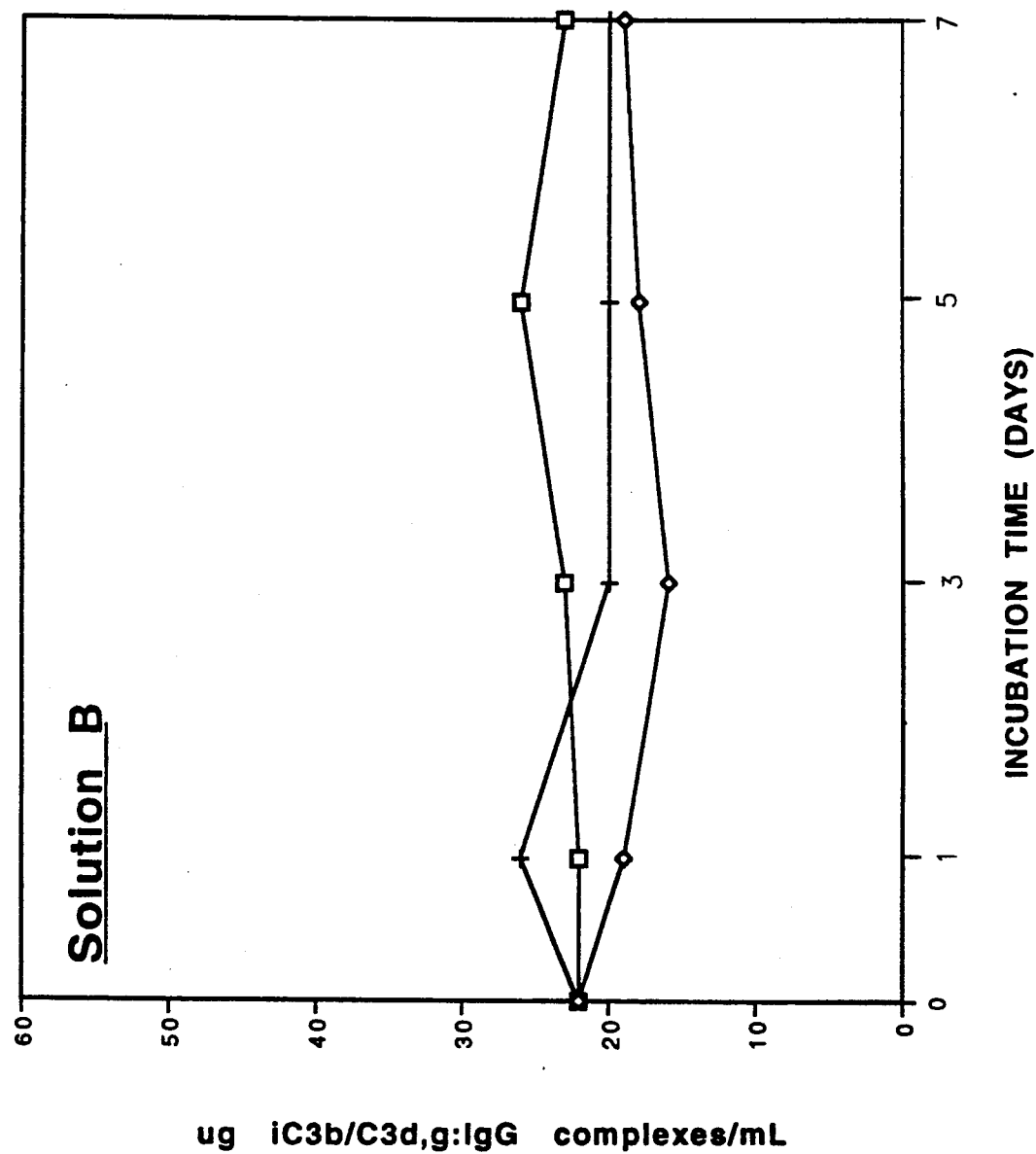

Also seen in FIG. 11 is the observation that untreated EDTA-plasma samples could be stored at 4° C. for as long as 7 days without appreciable change in analyte levels detected by the RCR CIC EIA. And, as also evident from the data presented in FIG. 19, the CIC analyte levels detectable in the RCR CIC EIA decrease with increasing time of storage at 22° C. in an untreated EDTA-NHP sample, containing either normal or abnormally elevated levels of CIC. This decrease in RCR CIC EIA signal is due to the spontaneous activation of C with the resultant production of iC3b and C3d,g physiological breakdown fragments of C3 Which compete for the CIC binding sites on the MoAb 013III-31.4.3.2.2 coated microtiter wells.

The results presented in FIG. 11 also clearly indicated that premixing an EDTA-NHP patient plasma sample with an equal volume of Solution B allowed for sample storage at −20° C., 4° C. or 22° C. for a minimum of 7 days without evidence of spontaneous C3 activation.

Figure 12A:
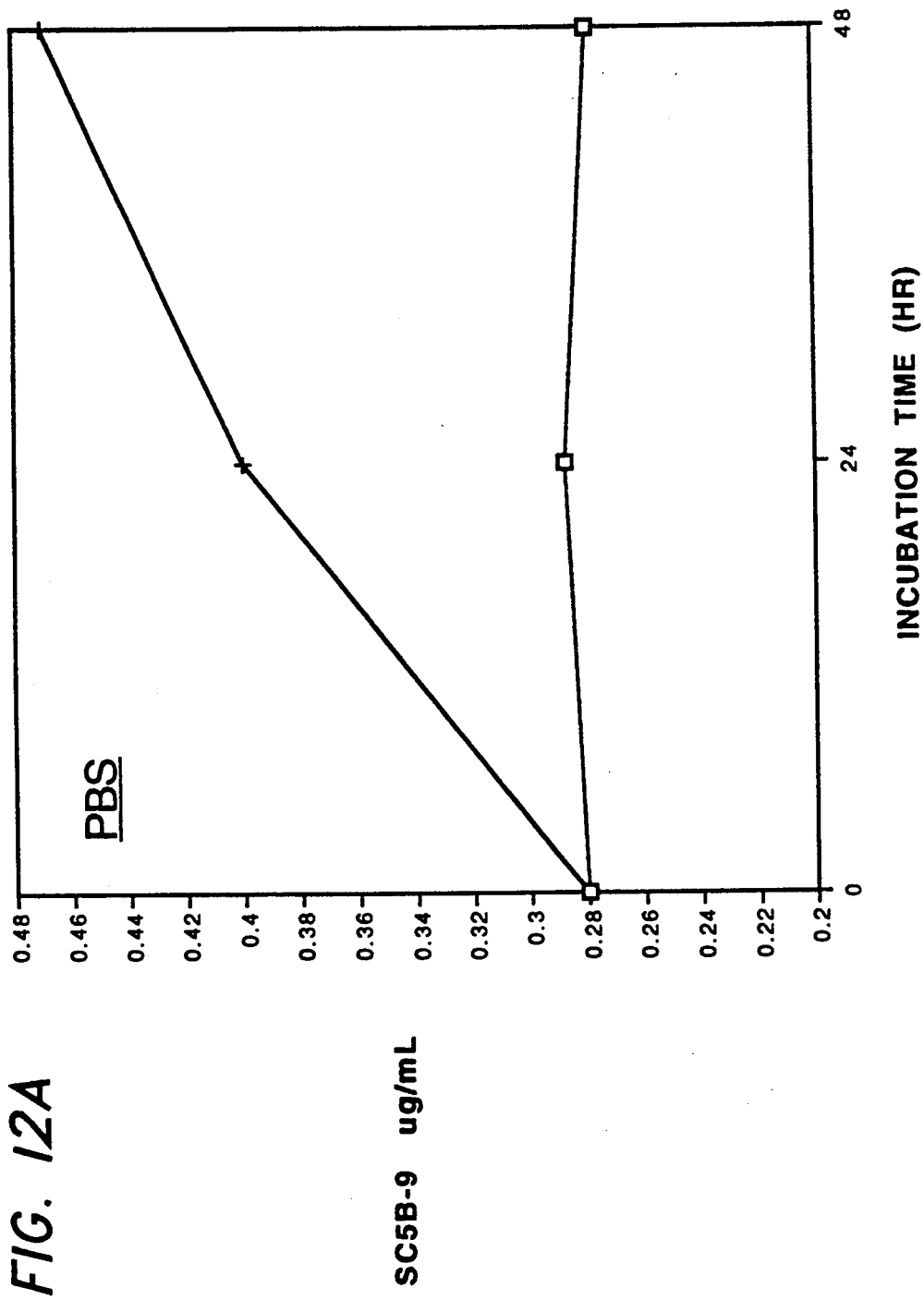
FIGS. 12A and 12B. Prevention of spontaneous terminal complement component activation, i.e., C5 through C9, in EDTA normal human plasma. EDTA-NHP was mixed with an equal volume of PBS (FIG. 12A) or Solution B (FIG. 12B) and stored at 4° C. or 22° C. After the time periods indicated, samples were collected and stored at −70° C. the collected samples were thawed all at once and spontaneous terminal complement pathway activation was quantitated using the SC5b-9 complex EIA. The results are shown as µg SC5b-9/mL present in each experimental plasma sample as a function of time. Incubation conditions: 4° C. (open square symbols); 22° C. (plus (+) symbols).
Figure 12B:
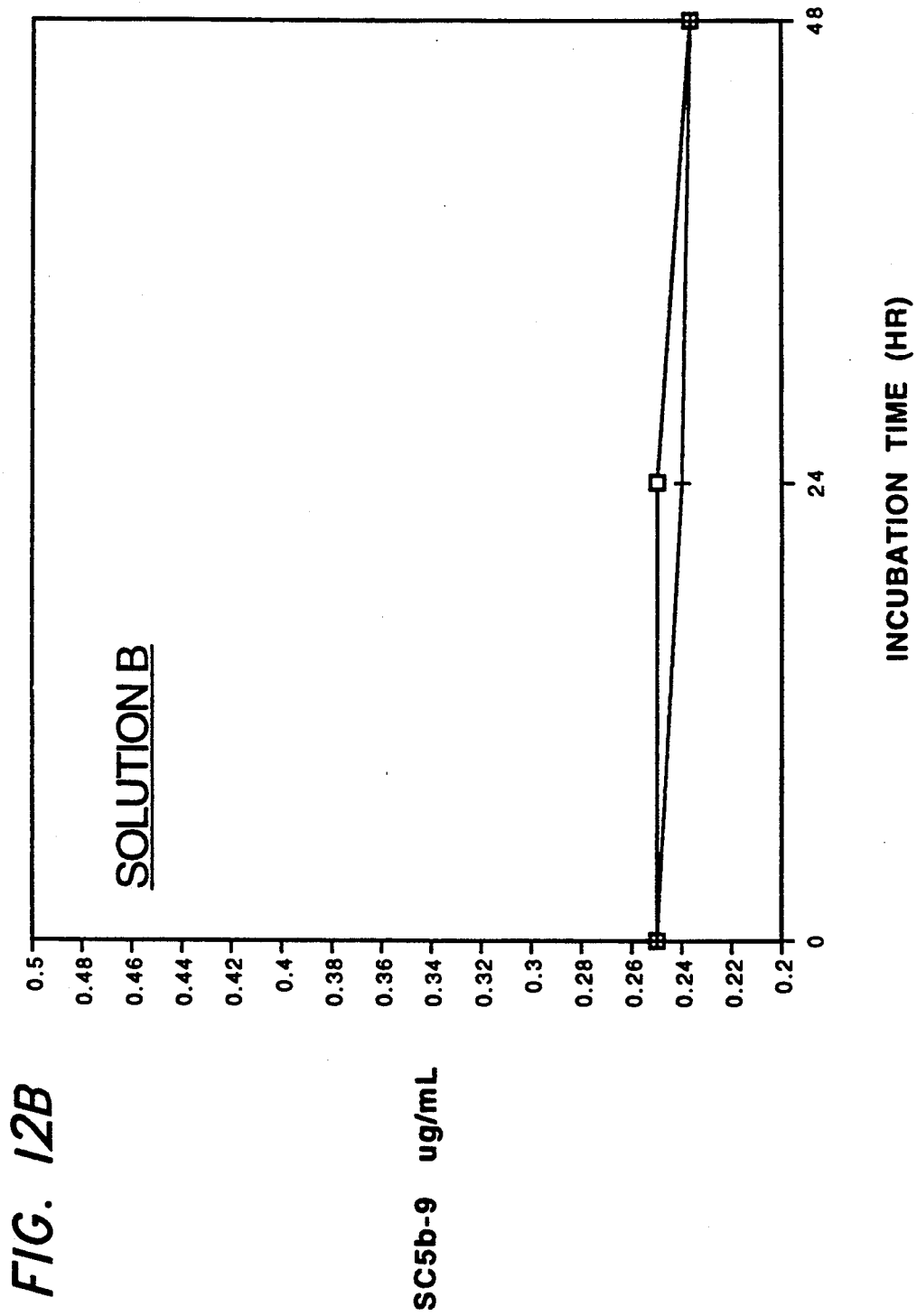

FIG. 12 illustrates the use of the preferred embodiment of the invention in the prevention of the spontaneous activation of the terminal complement components C5 through C9 in a complement-containing sample stored in vitro. For this experiment, freshly drawn EDTA-NHP was mixed with an equal volume of PBS or Solution B and stored at 4° C. or 22° C. After the time periods indicated, samples were collected and stored at −70° C. The collected samples were thawed all at once and C5 through C9 spontaneous activation was quantitated using the SC5b-9 EIA. Untreated EDTA-NHP could be stored at 4° C. for as long as 48 hr without any evidence of spontaneous activation of the terminal complement components. However, untreated EDTA-NHP samples stored at 22° C. showed significant levels of spontaneous SC5b-9 complex formation after 24 hr storage. In contrast, when EDTA-NHP was mixed with Solution B before storage, spontaneous SC5b-9 complex formation was completely inhibited upon storage at 4° C. or 22° C. for a minimum of 48 hr.

It should be apparent from the foregoing that other polyhydroxyl compounds can be substituted in the Examples to obtain similar results. Accordingly, the invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced with their scope.

What is claimed:

1. A method for determining the concentration of a complement protein or a fragment thereof in a sample, comprising the steps of:

adding an effective, spontaneous complement activation-preventive amount of a polyhydroxyl compound or a mixture of said compounds, selected from the group consisting o monosaccharides, disaccharides, oligosaccharides, or amine or alcohol derivatives thereof, to said sample; and assaying the sample to determine the concentration therein of a complement protein or a fragment thereof.

2. A method according to claim 1, further comprising storing said sample at a temperature below 30° C., whereby spontaneous activation of complement is said sample is prevented for at least 48 hours.

3. A method according to claim 1, wherein said polyhydroxyl compound is β-D-glucose.

4. A method according to claim 1, wherein said polyhydroxyl compound is sucrose.

5. A method according to claim 1, wherein said polyhydroxyl compound is trehalose.

6. A method according to claim 1, wherein said polyhydroxyl compound is gentiobiose.

7. A method according to claim 1, wherein said saccharide is melibiose.

8. A method according to claim 1, wherein said adding step further comprises the addition of an effective amount of a divalent cation chelator.

9. A method according to claim 8, wherein said divalent cation chelator is ethylene diamine tetraacetic acid (EDTA).

10. A method according to claim 1, wherein the activation of complement proteins that release C4d, C3a, iC3b, C3d, or Bb activation fragments as well as SC5b-9complex is prevented.

11. A method according to claim 1, wherein the activation of complement proteins that release C4a, C5a, and Ba activation fragments is prevented.

12. A method according to claim 1 wherein said complement-containing sample is from an animal.

13. A method according to claim 12 wherein the complement-containing sample is from a vertebrate animal.

14. A method according to claim 13 wherein the complement-containing sample is from a mammal.

15. A method according to claim 12 wherein said sample is a physiological fluid.

16. A method according to claim 15 wherein said sample is whole blood and said method further comprises the addition of an effective amount of an anticoagulant.

17. A method according to claim 1 wherein effective amounts of said polyhydroxyl compound, a divalent cation chelator, and an anticoagulant are present within an evacuated chamber into which a volume of whole blood is drawn.

18. A method according to claim 16 or 17, wherein said anticoagulant is heparin.

19. A method according to claim 1, further comprising the step of storing the sample at a temperature below about 30° C. for a period of between at least 4 hours and 7 days, prior to the assay step.

20. A method according to claim 1, wherein the concentration of a complement protein or a fragment thereof is determined by an immunoassay procedure.

21. A method according to claim 1, wherein the concentration of a complement protein or a fragment thereof is determined by an enzyme immunoassay procedure.

22. A method according to claim 1, wherein said sample comprises blood or a fraction thereof.

* * * * *